United States Patent
Bardelli et al.

(10) Patent No.: US 11,015,225 B2
(45) Date of Patent: *May 25, 2021

(54) METHOD OF TREATING CANCER BASED ON IDENTIFYING MUTATIONS IN THE EXTRACELLULAR DOMAIN III OF EPIDERMAL GROWTH FACTOR RECEPTOR GENE

(71) Applicants: FUNDACIÔ INSTITUT MAR D'INVESTIGACIONS MÈDIQUES (IMIM), Barcelona (ES); Alberto Bardelli, Turin (IT); Sabrina Arena, Turin (IT)

(72) Inventors: Alberto Bardelli, Turin (IT); Sabrina Arena, Turin (IT); Clara Montagut Viladot, Barcelona (ES); Joan Albanell Mestres, Barcelona (ES); Ana Rovira Guerin, Barcelona (ES); Beatriz Bellosillo Paricio, Barcelona (ES); Alba Dalmases Massegú, Barcelona (ES)

(73) Assignees: Alberto Bardelli, Turin (IT); Sabrina Arena, Turin (IT); FUNDACIÓ INSTITUT MAR D'INVESTIGACIONS MEDIQUES (IMIM), Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/500,007

(22) PCT Filed: Dec. 30, 2014

(86) PCT No.: PCT/EP2014/079477
§ 371 (c)(1),
(2) Date: Jan. 27, 2017

(87) PCT Pub. No.: WO2016/015788
PCT Pub. Date: Feb. 4, 2016

(65) Prior Publication Data
US 2017/0260250 A1    Sep. 14, 2017

(30) Foreign Application Priority Data
Jul. 28, 2014   (EP) .................................... 14382288

(51) Int. Cl.
*C12Q 1/6827* (2018.01)
*C12Q 1/6886* (2018.01)
*G01N 33/574* (2006.01)
*G01N 33/74* (2006.01)
*C07K 14/71* (2006.01)

(52) U.S. Cl.
CPC ............ *C12Q 1/6886* (2013.01); *C07K 14/71* (2013.01); *G01N 33/57419* (2013.01); *G01N 33/74* (2013.01); *C12Q 2600/106* (2013.01); *C12Q 2600/156* (2013.01); *G01N 2333/485* (2013.01); *G01N 2333/71* (2013.01); *G01N 2800/52* (2013.01)

(58) Field of Classification Search
CPC ..................... G01N 33/57484; G01N 2800/52
See application file for complete search history.

(56) References Cited

U.S. PATENT DOCUMENTS 5,914,269 A  *  6/1999  Bennett .............. C12N 15/1138
435/375

FOREIGN PATENT DOCUMENTS

| WO | WO2013/017645 | * | 2/2013 |
| WO | WO 2013/017645 A1 | | 2/2013 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Sanchez-Martin (Clinical Cancer Research, vol. 22, No. 13, p. 3260-3267, 2016) (Year: 2016).*
Rychlik (Nucleic Acids Research, vol. 17, No. 21, p. 8543-8551, 1989) (Year: 1989).*
Buck (Biotechniques, vol. 27, p. 528-536, 1999) (Year: 1999).*
Arena et al., "Emergence of Multiple EGFR Extracellular Mutations during Cetuximab Treatment in colorectal cancer", Clinical Cancer Research Biology of Human Tumors May 2015, Jan. 26, 2015, vol. 21 No. 9, pp. 2157-2166, 11 pages.
Montagut et al., "Efficacy of Sym004 in patients with metastiatic colorectal cancer with acquired resistance to Anti-EGFR therapy and molecularly selected by circulating tumor DNA analyses, A Phase 2 Randomized Clinical Trial", JAMA Oncology 2018, Feb. 8, 2018, vol. 4, No. 4, pp. E1-E9, 9 pages.
Strickler et al., "Genomic Landscape of Cell-Free DNA in patients with colorectal cancer", Cancer Discovery Feb. 2018 (e-published Dec. 1, 2017), vol. 8, pp. 164-173, 11 pages.

(Continued)

Primary Examiner — Michael Allen
(74) Attorney, Agent, or Firm — Squire Patton Boggs (US) LLP

(57) ABSTRACT

The invention relates to new identified mutations in the epidermal growth factor receptor gene, leading to amino acidic changes which highly correlate with the resistance to a therapy regimen comprising cetuximab. The invention includes peptide sequences and primers to detect the mutations, as well as kits for predicting the response of a subject to a therapy regime comprising cetuximab. In particular, the invention is useful in the therapy regimen applicable to metastasic colorectal cancer.

12 Claims, 6 Drawing Sheets
Specification includes a Sequence Listing.

(56) References Cited

OTHER PUBLICATIONS

Bardelli et al., "The road to resistance: EGFR mutation and cetuximab", Nature Medicine, Feb. 2012, vol. 18 No. 2, pp. 199-200, 2 pages.

Custodio et al., "Prognostic and predictive biomarkers for epidermal growth factor receptor-targeted therapy in colorectal cancer: Beyond KRAS mutations", Critical reviews in oncology/hematology, Jan. 1, 2013, vol. 85, No. 1, pp. 45-81, 37 pages.

Diaz et al. "The molecular evolution of acquired resistance to targeted EGFR blockade in colorectal cancers", Nature, Jun. 2012, vol. 486, pp. 537-540, 4 pages.

Eisenhauer et al., "New response evaluation criteria in solid tumours: Revised RECIST guideline (Version 1.1)", Eur Journal Cancer, 2009, vol. 45, No. 2, pp. 228-247, 20 pages.

Karapetis et al., "K-ras Mutations and Benefit from Cetuximab in Advanced Colorectal Cancer", The New England Journal of Medicine, Oct. 2008, vol. 359. No. 17, pp. 1757-1765, 9 pages.

Lynch et al., "Activating mutations in the epidermal growth factor receptor underlying responsiveness of non-small-cell lung cancer to Gefitinib", The New England Journal of Medicine, May 2004, vol. 350, No. 21, pp. 2129-2139, 11 pages.

Mendelsohn et al., "Status of Epidermal Growth Factor Receptor Antagonists in the Biology and Treatment of Cancer ", Journal of Clinical Oncology, 2003, vol. 21, No. 14, pp. 2787-2799, 13 pages.

Misale et al., "Emergence of KRAS mutations and acquired resistance to anti-EGFR therapy in colorectal cancer", Nature, Jun. 2012, vol. 486, pp. 532-536, 7 pages.

Misale et al., "Blockade of EGFR and MEK Intercepts Heterogeneous Mechanisms of acquired resistance to anti-EGFR therapies in colorectal cancer", Sci Transl Medicine, Feb. 2014, vol. 6, Issue 224, 224ra26, 12 pages.

Montagut et al., "Identification of a mutation in the extracellular domain of the Epidermal Growth Factor Receptor conferring cetuximab resistance in colorectal cancer", Nature Medicine, Jan. 22, 2012, vol. 18, No. 2, pp. 221-223, 4 pages.

Salido et al., "Increased ALK gene copy number and amplification are frequent in non-small cell lung cancer", J Thorac Oncol, Jan. 2011, vol. 6, No. 1, pp. 21-27, 15 pages.

Voigt et al., "Functional Dissection of the Epidermal Growth Factor Receptor Epitopes Targeted by Panitumumab and Cetuximab 1,2", Neoplasia, Nov. 2012, vol. 14, No. 11, pp. 1023-1031, 11 pages.

Yuan et al., "The prognostic role of BRAF mutation in metastatic colorectal cancer receiving anti-EGFR monoclonal antibodies: A Meta-Analysis", Plos One, Jun. 11, 2013, vol. 8, Issue 6, pp. e65995, 10 pages.

International Search Report and Written Opinion dated Mar. 11, 2015 for PCT/EP2014/079477, 11 pages.

\* cited by examiner (A)

A>C
AAA>ACA
Lys>Thr
K467T (B)

C>T
CGC>TGC
Arg>Cys
R451C (A)

(B)

(A)

(B)
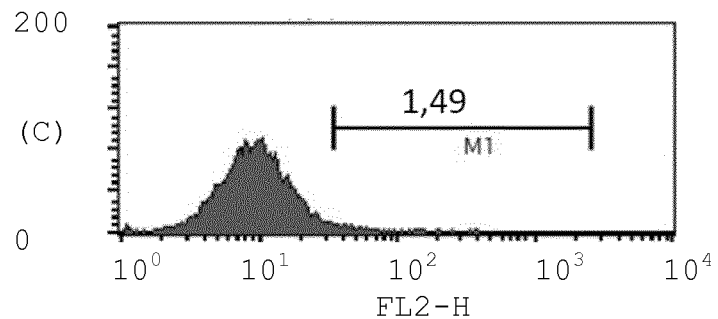
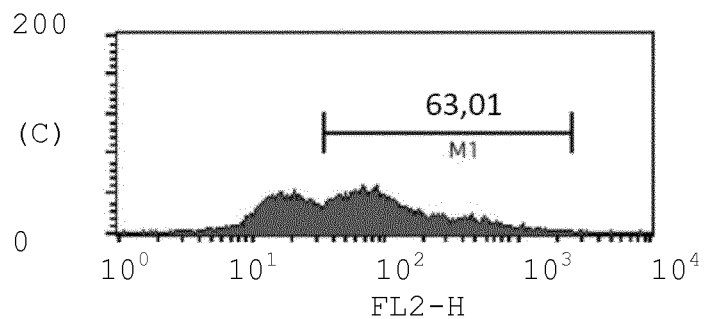
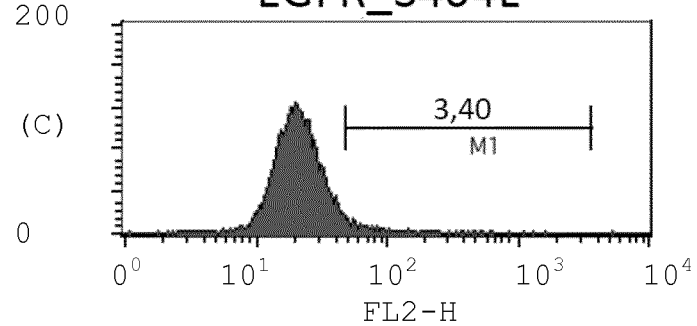
Cont. FIG. 3

(A)

(B)
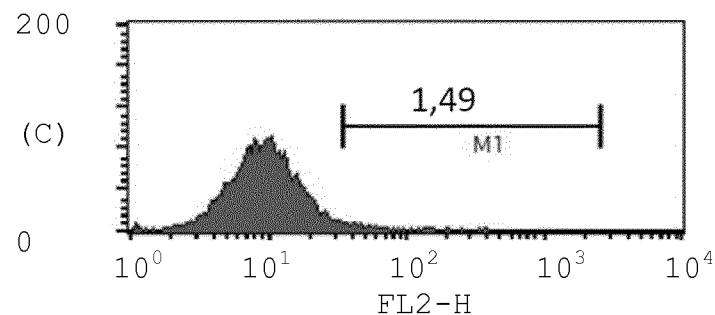
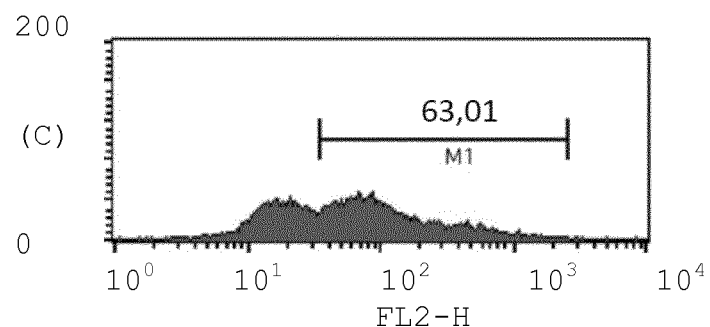
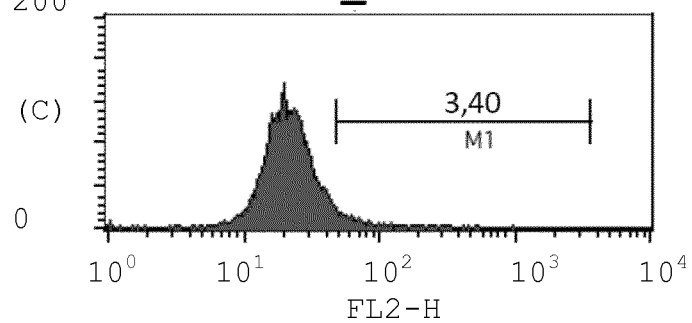
Cont. FIG. 4

SEQUENCE LISTING

<160> NUMBER OF SEQ ID NOS: 14

<210> SEQ ID NO 1
<211> LENGTH: 17
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is an amino acid selected from arginine (R)
      and cysteine (C)
<220> FEATURE:
<221> NAME/KEY: VARIANT
<222> LOCATION: (17)..(17)
<223> OTHER INFORMATION: X is an amino acid selected from lysine (K) and
      threonine (T)

<400> SEQUENCE: 1

Xaa Ser Leu Lys Glu Ile Ser Asp Gly Asp Val Ile Ile Ser Gly Asn
1               5                   10                  15

Xaa

<210> SEQ ID NO 2
<211> LENGTH: 1210
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp

-continued

```
                245                 250                 255
Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670
```

```
Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
            770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                1005

Asp Val Val Asp Ala Asp Glu  Tyr Leu Ile Pro Gln  Gln Gly Phe
1010                1015                1020

Phe Ser Ser Pro Ser Thr Ser  Arg Thr Pro Leu Leu  Ser Ser Leu
1025                1030                1035

Ser Ala Thr Ser Asn Asn Ser  Thr Val Ala Cys Ile  Asp Arg Asn
1040                1045                1050

Gly Leu Gln Ser Cys Pro Ile  Lys Glu Asp Ser Phe  Leu Gln Arg
1055                1060                1065

Tyr Ser Ser Asp Pro Thr Gly  Ala Leu Thr Glu Asp  Ser Ile Asp
1070                1075                1080
```

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 3
<211> LENGTH: 5616
<212> TYPE: DNA
<213> ORGANISM: Homo sapiens

<400> SEQUENCE: 3

| | | | | |
|---|---|---|---|---|
| ccccggcgca gcgcggccgc agcagcctcc gcccccgca cggtgtgagc gcccgacgcg | 60 |
| gccgaggcgg ccggagtccc gagctagccc cggcggccgc cgccgcccag accggacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcactttga agatcatttt ctcagcctcc agaggatgtt caataactgt | 420 |
| gaggtggtcc ttgggaattt ggaaattacc tatgtgcaga ggaattatga tcttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caaccctgc cctgtgcaac | 720 |
| gtggagagca tccagtggcg ggacatagtc agcagtgact ttctcagcaa catgtcgatg | 780 |
| gacttccaga accacctggg cagctgccaa aagtgtgatc caagctgtcc caatgggagc | 840 |
| tgctgggggt caggagagga gaactgccag aaactgacca aaatcatctg tgcccagcag | 900 |
| tgctccgggc gctgccgtgg caagtccccc agtgactgct gccacaacca gtgtgctgca | 960 |
| ggctgcacag gcccccggga gagcgactgc ctggtctgcc gcaaattccg agacgaagcc | 1020 |
| acgtgcaagg acacctgccc ccactcatg ctctacaacc ccaccacgta ccagatggat | 1080 |
| gtgaaccccg aggcaaata cagctttggt gccacctgcg tgaagaagtg tccccgtaat | 1140 |
| tatgtggtga cagatcacgg ctcgtgcgtc cgagcctgtg ggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |

-continued

```
ttcaaaaact gcacctccat cagtggcgat ctccacatcc tgccggtggc atttaggggt    1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag gcagggaatg cgtggacaag    1860
tgcaaccttc tggagggtga gccaaggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga cgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatcctctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga agaatgcat tgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaacccgcg    3600 cccagcagag acccacacta ccaggacccc cacagcactg cagtgggcaa ccccgagtat    3660
ctcaacactg tccagcccac ctgtgtcaac agcacattcg acagccctgc ccactgggcc    3720
```

```
cagaaaggca gccaccaaat tagcctggac aaccctgact accagcagga cttcttccc      3780 aaggaagcca agccaaatgg catctttaag ggctccacag ctgaaaatgc agaataccta     3840
agggtcgcgc cacaaagcag tgaatttatt ggagcatgac cacggaggat agtatgagcc     3900
ctaaaaatcc agactctttc gatacccagg accaagccac agcaggtcct ccatcccaac     3960
agccatgccc gcattagctc ttagacccac agactggttt tgcaacgttt acaccgacta     4020
gccaggaagt acttccacct cgggcacatt ttgggaagtt gcattccttt gtcttcaaac     4080
tgtgaagcat ttacagaaac gcatccagca agaatattgt cccttgagc agaaatttat      4140 ctttcaaaga ggtatatttg aaaaaaaaaa aagtatatg tgaggatttt tattgattgg      4200
ggatcttgga gttttcatt gtcgctattg atttttactt caatgggctc ttccaacaag      4260
gaagaagctt gctggtagca cttgctaccc tgagttcatc caggcccaac tgtgagcaag     4320
gagcacaagc cacaagtctt ccagaggatg cttgattcca gtggttctgc ttcaaggctt     4380
ccactgcaaa acactaaaga tccaagaagg ccttcatggc cccagcaggc cggatcggta     4440
ctgtatcaag tcatggcagg tacagtagga taagccactc tgtcccttcc tgggcaaaga    4500
agaaacggag gggatggaat tcttccttag acttactttt gtaaaaatgt ccccacggta     4560
cttactcccc actgatggac cagtggttc cagtcatgag cgttagactg acttgtttgt      4620
cttccattcc attgttttga aactcagtat gctgccctg tcttgctgtc atgaaatcag      4680
caagagagga tgacacatca ataataact cggattccag cccacattgg attcatcagc      4740
atttggacca atagcccaca gctgagaatg tggaatacct aaggatagca ccgcttttgt     4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920 acccccaaa attagtttgt gttacttatg gaagatagtt ttctcctttt acttcacttc     4980
aaaagctttt tactcaaaga gtatatgttc cctccaggtc agctgccccc aaacccctc     5040 cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaataatt tctctacaat tggaagattg      5280
gaagattcag ctagttagga gcccacctt tttcctaatc tgtgtgtgcc ctgtaacctg      5340
actggttaac agcagtcctt tgtaaacagt gttttaaact ctcctagtca atatccaccc    5400
catccaattt atcaaggaag aaatggttca gaaatatttt tcagcctaca gttatgttca    5460
gtcacacaca catacaaaat gttcctttg cttttaaagt aatttttgac tcccagatca      5520
gtcagagccc ctacagcatt gttaagaaag tatttgattt ttgtctcaat gaaataaaa     5580 ctatattcat ttccactcta aaaaaaaaa aaaaaa                              5616
```

<210> SEQ ID NO 4  
<211> LENGTH: 25  
<212> TYPE: PRT  
<213> ORGANISM: Homo sapiens  
<220> FEATURE:  
<221> NAME/KEY: VARIANT  
<222> LOCATION: (25)..(25)  
<223> OTHER INFORMATION: X is an amino acid selected from serine (S) and arginine (R)

<400> SEQUENCE: 4

Asn Leu Cys Tyr Ala Asn Thr Ile Asn Trp Lys Lys Leu Phe Gly Thr

```
                1               5                   10                  15
Ser Gly Gly Lys Thr Lys Ile Ile Xaa
                20                  25

<210> SEQ ID NO 5
<211> LENGTH: 42
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is an amino acid selected from arginine (R)
      and cysteine (C)
<220> FEATURE:
<221> NAME/KEY: VARIANT
<222> LOCATION: (17)..(17)
<223> OTHER INFORMATION: X is an amino acid selected from lysine (K) and
      threonine (T)
<220> FEATURE:
<221> NAME/KEY: VARIANT
<222> LOCATION: (42)..(42)
<223> OTHER INFORMATION: X is an amino acid selected from arginine (R)
      and lysine (K)

<400> SEQUENCE: 5

Xaa Ser Leu Lys Glu Ile Ser Asp Gly Asp Val Ile Ile Ser Gly Asn
1               5                   10                  15

Xaa Asn Leu Cys Tyr Ala Asn Thr Ile Asn Trp Lys Lys Leu Phe Gly
                20                  25                  30

Thr Ser Gly Gly Lys Thr Lys Ile Ile Xaa
            35                  40

<210> SEQ ID NO 6
<211> LENGTH: 27
<212> TYPE: DNA
<213> ORGANISM: Artificial
<220> FEATURE:
<223> OTHER INFORMATION: Forward primer

<400> SEQUENCE: 6
caaagttttc agggatacat tgttttt                                          27

<210> SEQ ID NO 7
<211> LENGTH: 26
<212> TYPE: DNA
<213> ORGANISM: Artificial
<220> FEATURE:
<223> OTHER INFORMATION: Reverse primer

<400> SEQUENCE: 7
ttaaatggga atagcccttc aatatt                                           26

<210> SEQ ID NO 8
<211> LENGTH: 17
<212> TYPE: PRT
<213> ORGANISM: Homo sapiens

<400> SEQUENCE: 8

Arg Ser Leu Lys Glu Ile Ser Asp Gly Asp Val Ile Ile Ser Gly Asn
1               5                   10                  15

Thr

<210> SEQ ID NO 9
<211> LENGTH: 17
<212> TYPE: PRT
<213> ORGANISM: Homo sapiens
```

-continued

<400> SEQUENCE: 9

Cys Ser Leu Lys Glu Ile Ser Asp Gly Asp Val Ile Ile Ser Gly Asn
1               5                   10                  15

Thr

<210> SEQ ID NO 10
<211> LENGTH: 17
<212> TYPE: PRT
<213> ORGANISM: Homo sapiens

<400> SEQUENCE: 10

Cys Ser Leu Lys Glu Ile Ser Asp Gly Asp Val Ile Ile Ser Gly Asn
1               5                   10                  15

Lys

<210> SEQ ID NO 11
<211> LENGTH: 355
<212> TYPE: DNA
<213> ORGANISM: Homo sapiens

<400> SEQUENCE: 11
caaagttttc agggatacat tgttttata ttttcaccac atgatttttc ttctctccaa      60
tgtagtggtc agttttctct tgcagtcgtc agcctgaaca taacatcctt gggattacgc     120
tccctcaagg agataagtga tggagatgtg ataatttcag gaaacaaaaa tttgtgctat     180
gcaaatacaa taaactggaa aaaactgttt gggacctccg gtcagaaaac caaaattata     240
agcaacagag gtgaaaacag ctgcagtaag tcaccgcttt ctgtttagtt tatggagttg     300
gttctaatgg gtcctttatt tgtatttaga atattgaagg gctattccca tttaa          355

<210> SEQ ID NO 12
<211> LENGTH: 21
<212> TYPE: PRT
<213> ORGANISM: Homo sapiens

<400> SEQUENCE: 12

Leu Arg Ser Leu Lys Glu Ile Ser Asp Gly Asp Val Ile Ile Ser Gly
1               5                   10                  15

Asn Lys Asn Leu Cys
            20

<210> SEQ ID NO 13
<211> LENGTH: 17
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is an amino acid selected from arginine (R)
      and cysteine (C)
<220> FEATURE:
<221> NAME/KEY: VARIANT
<222> LOCATION: (14)..(14)
<223> OTHER INFORMATION: X is an amino acid selected from serine (S) and
      leucine (L)
<220> FEATURE:
<221> NAME/KEY: VARIANT
<222> LOCATION: (15)..(15)
<223> OTHER INFORMATION: X is an amino acid selected from glycine (G)
      and arginine (R)
<220> FEATURE:
<221> NAME/KEY: VARIANT
<222> LOCATION: (17)..(17)
<223> OTHER INFORMATION: X is an amino acid selected from lysine (K) and threonine (T)

<400> SEQUENCE: 13

Xaa Ser Leu Lys Glu Ile Ser Asp Gly Asp Val Ile Ile Xaa Xaa Asn
1               5                   10                  15

Xaa

<210> SEQ ID NO 14
<211> LENGTH: 42
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is an amino acid selected from arginine (R)
      and cysteine (C)
<220> FEATURE:
<221> NAME/KEY: VARIANT
<222> LOCATION: (14)..(14)
<223> OTHER INFORMATION: X is an amino acid selected from serine (S) and
      leucine (L)
<220> FEATURE:
<221> NAME/KEY: VARIANT
<222> LOCATION: (15)..(15)
<223> OTHER INFORMATION: X is an amino acid selected from glycine (G)
      and arginine (R)
<220> FEATURE:
<221> NAME/KEY: VARIANT
<222> LOCATION: (17)..(17)
<223> OTHER INFORMATION: X is an amino acid selected from lysine (K) and
      threonine (T)
<220> FEATURE:
<221> NAME/KEY: VARIANT
<222> LOCATION: (42)..(42)
<223> OTHER INFORMATION: X is an amino acid selected from serine (S) and
      arginine (R)

<400> SEQUENCE: 14

Xaa Ser Leu Lys Glu Ile Ser Asp Gly Asp Val Ile Ile Xaa Xaa Asn
1               5                   10                  15

Xaa Asn Leu Cys Tyr Ala Asn Thr Ile Asn Trp Lys Lys Leu Phe Gly
            20                  25                  30

Thr Ser Gly Gly Lys Thr Lys Ile Ile Xaa
            35                  40

METHOD OF TREATING CANCER BASED ON IDENTIFYING MUTATIONS IN THE EXTRACELLULAR DOMAIN III OF EPIDERMAL GROWTH FACTOR RECEPTOR GENE

CROSS-REFERENCE TO RELATED APPLICATION

This application is a U.S. national phase entry of International Patent Application No. PCT/EP2014/079477, filed Dec. 30, 2014, which claims priority to European Patent Application No. 1438228.0, filed Jul. 28, 2014. Each of the foregoing applications is incorporated herein by reference in its entirety.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "P2949PC00_SEQ_LIST_dec2014_ST25.txt," created Dec. 30, 2014, and is 23,323 bytes in size. The sequence listing contained in this .txt file is part of the specification and is incorporated herein by reference in its entirety.

The present invention is directed to new mutations of the human epidermal growth factor receptor gene, as a marker for determining response to monoclonal antibody treatment.

BACKGROUND ART

Epidermal growth factor receptor gene (EGFR) is a transmembrane tyrosine-kinase receptor that belongs to the epidermal growth factor family of receptors (ErbB family), which includes four closely related receptor tyrosine kinases: EGFR (ErbB-1), HER2/c-neu (ErbB-2), Her 3 (ErbB-3) and Her 4 (ErbB-4). Upon ligand binding, EGFR activates intracellular signalling pathways, mainly the RAS-RAF-MEK-ERK cascade and the PI3K-AKT pathway, that regulate key oncogenic events such as apoptosis, cell growth, angiogenesis and metastasis. Aberrant activation or overexpression of EGFR has been reported in several types of cancer (i.e. Mendelsohn J, Baselga J et al., "Epidermal growth factor receptor targeting in cancer". Semin Oncol—2006, Vol. 33, pp.: 369-38). Mutations in EGFR gene have been described in lung cancer. Examples of such mutations are disclosed for instance in the document of Lynch T J et al., "Activating mutations in the epidermal growth factor receptor underlying responsiveness of non-small-cell lung cancer to gefitinib", N Engl J Med-2004, Vol. 350, pp: 2129-2139.

Metastasic colorectal cancer (mCRC) is the second leading cause of death from cancer in the Western Countries world.

A therapy based on monoclonal antibodies (moAbs), e.g. cetuximab and panitumumab, which are directed against the extracellular domain III of EGFR, provides significant survival benefit to patients with mCRC and are now standard components of therapy regimens for these patients, i.e. either alone or in combination with other antineoplastic drug(s).

The moAbs bind to foreign antigens expressed on cancer cells. Once bound, the cancer cells are marked for destruction by the patient's immune system. In addition to targeting cancer cells, moAbs can be designed to act on other cell types and molecules necessary for tumor growth. For example, antibodies can neutralize growth factors and thereby inhibit tumor expansion. It is possible to create a moAb specific to almost any extracellular/cell surface target (such as cancer cells). In summary, moAbs can be used to destroy malignant tumor cells and prevent tumor growth by blocking specific cell receptors. Therapeutic moAbs cetuximab and panitumumab bind to EGFR and prevent the activation of intracellular signalling pathways driven by EGFR (i.e., the RAS-RAF-MEK-ERK cascade and PI3K-AKT pathway).

Not all patients with mCRC respond to a therapy regimen comprising moAbs. The lack of response of a patient with mCRC to such a treatment could be primary (i.e. since the beginning of anti-EGFR moAb treatment), known as primary resistance. Moreover, all mCRC patients that initially respond to anti-EGFR moAbs invariably develop secondary resistance, i.e. acquired resistance to anti-EGFR moAb. In both cases, the result is treatment failure.

The mechanisms that contribute to the acquisition of such treatment resistance in mCRC patients is not fully known yet.

KRAS (also known as V-Ki-ras2 Kirsten rat sarcoma viral oncogene homolog) is an EGFR downstream effector, and a marker of primary resistance to anti-EGFR moAbs. KRAS has a significant impact on the optimization of treatment of mCRC patients. Forty percent of colorectal tumors harbour a mutation in the KRAS gene and these patients do not benefit from anti-EGFR moAbs. In current clinical practice all mCRC patients who are being considered for anti-EGFR moAb therapy should undergo KRAS testing, and patients should be excluded from cetuximab or panitumumab therapy if a KRAS mutation is detected.

While the use of KRAS mutations and more recently NRAS (Neuroblastomas Ras viral oncogene homolog) mutations as markers of primary resistance to anti-EGFR moAbs has meant a significant step towards optimization of treatment of mCRC patients, the understanding of molecular changes underlying acquired resistance to anti-EGFR moAb is currently a crucial challenge to improve the clinical benefit of these drugs. Recently, mechanisms of secondary resistance (acquired resistance) have been elucidated in patients. The most common event is the emergence of KRAS mutations or gene amplification in approximately 50% of the cases, as deducible from Misale et al., "Emergence of KRAS mutations and acquired resistance to anti-EGFR therapy in colorectal cancer", Nature—2012, Vol. No. 486, pp.: 532-536.

Other mechanisms of secondary resistance include acquisition of a mutation in the extracellular domain of EGFR abrogating binding of cetuximab to EGFR, as illustrated by Montagut et al., "Identification of a mutation in the extracellular domain of the Epidermal Growth Factor Receptor conferring cetuximab resistance in colorectal cancer", Nature Medicine—2012, Vol. No. 18, pp.:221-223. The mutation is the polymorphism in the extracellular portion of the EGFR gene, resulting in the amino acid substitution S492R at domain III of the codified protein.

With the aim of studying monoclonal antibody interaction with EGFR epitopes, several reports are directed to the mapping of critical epitopes. These reports provide data of mutations obtained by site-directed mutagenesis at domain III of EGFR. An example of these reports is the one of Voigt et al., "Functional Dissection of the Epidermal Growth Factor Receptor Epitopes Targeted by Panitumumab and Cetuximab", Neoplasia—2012, Vol. No. 14(11), pp.: 1023-1031. This document discloses mutations in which the wild-type amino acid has been mostly changed by an alanine, according to the protocols and tools of site-mutagenesis assays. Voigt concludes that in-vitro data from site-mutagenesis may not be meaningful in vivo because residues defined as critical for cetuximab or panitumumab binding by an alanine scanning approach may well be mutated in vivo to other amino acids without functional consequences. Therefore, those key positions in a defined epitope identified by site-mutagenesis do not suggest the in vivo meaningful mutation (the particular amino acid exchange).

Drug resistance is then a major challenge in colorectal cancer patients treated with anti-EGFR drugs, namely cetuximab and panitumumab. Elucidation of the molecular mechanisms of resistance represents a great goal, but this implies detection of meaningful mutations or other gene alterations as markers for predicting a response and, at the same time, for determining if a particular medical regimen has to be modified due to acquired resistance (secondary resistance). In summary, the state of the art provides useful tools for detecting primary and secondary resistance to anti-EGFR moAb therapies in patients with mCRC, but it is necessary to identify additional and alternative predictive biomarkers of resistance in order to cover patients with different mutations, or with a different evolution of the resistance molecular mechanisms.

SUMMARY OF THE INVENTION

The inventors have identified new mutations in the extracellular domain of human EGFR (domain III) that correlate with resistance to the treatment with some moAbs used in the cancer therapy. The mutations lead to the amino acid substitutions of an arginine by a cysteine at position 451 of the EGFR protein; of a serine by a leucine at position 464 of the EGFR; of a glycine by an arginine at position 465 of the EGFR protein; and of a lysine by a threonine at position 467 of the EGFR protein.

Wild type human EGFR protein has the amino acid sequence SEQ ID NO: 2, and the mutations are known herein as R451C, S464L, G465R and K467T. Mutations may be detected alone or in combination with each of the others in patients with mCRC after treatment with anti-EGFR moAbs.

All these mutations are located in a particular amino acid sequence fragment of the cetuximab binding epitope. Namely, they are located in a fragment from amino acid at position 450 to amino acid at position 470 of SEQ ID NO: 2, this SEQ ID NO: 2 corresponding to the consensus wild-type amino acid sequence of human EGFR, This amino acid sequence fragment of the cetuximab binding epitope is herewith referred also as SEQ ID NO: 12 (LRSLKEISDGD-VIISGNKNLC). Interestingly, inventors discovered that this fragment includes many of the particular amino acid exchanges (mutations) that lead to a real impairment (i.e not effectivity) of many anti-EGFR moAb treatments. As above exposed, many amino acid positions have been determined as key positions by mutagenesis while mapping anti-EGFR-moAb binding sites, nonetheless, it is also known that mapping assays are not conclusive for determining resistance to treatments.

Therefore, the inventors provide for the first time a fragment of the extracellular domain III of EGFR that contains or summarizes many mutation points with a real effect on therapy. Analysing or determining the sequence within this fragment (SEQ ID NO: 12) provides the advantage of detecting many of the possibly resistant patients to treatments including anti-EGFR moAb. Examples of amino acids within this SEQ ID NO: 12 (LRSLKEISDGDVIISGNKNLC) that lead to resistance to the widely employed anti-EGFR moAb cetuximab are indicated in bold and underwritten.

All these mutations are located in exon 12 of the mRNA variant 1 of the human EGFR gene finally coding for EGFR protein of SEQ ID NO: 2. In addition, all of them relate to a change of wild-type amino acids to bulky amino acids (i.e. those with a side-chain consisting of branched or unbranched C1-C4 hydrocarbons, optionally with a terminal amino group) and/or polar or charged amino acids. In particular, most of the mutations relate to a change of a polar and/or charged amino acid with a side-chain comprising a terminal amino (—NH2). More in particular, two of the mutations relate to a change of an amino acid with a side-chain comprising a terminal amino (—NH2). In addition, mutations R451C and K467T imply the substitution of an amino acid with a side-chain comprising a terminal amino (—NH2) for a polar amino acid, whose carbohydrate side-chain comprises radicals with atoms from the oxygen group, namely —OH and —SH, and they have a similar chain size as depicted below:

$$H_2N-CHC(=O)-OH$$
$$|$$
$$CH_2$$
$$|$$
$$CH_2$$
$$|$$
$$CH_2$$
$$|$$
$$NH$$
$$|$$
$$C=NH$$
$$|$$
$$NH_2$$

Arg, R $$H_2N-CHC(=O)-OH$$
$$|$$
$$CH_2$$
$$|$$
$$CH_2$$
$$|$$
$$CH_2$$
$$|$$
$$CH_2$$
$$|$$
$$NH_2$$

Lys, K $$H_2N-CHC(=O)-OH$$
$$|$$
$$CHOH$$
$$|$$
$$CH_3$$

Thr, T $$H_2N-CHC(=O)-OH$$
$$|$$
$$CH_2$$
$$|$$
$$SH$$

Cys, C

Thus, inventors provide for the first time the association of mutations in domain III of human EGFR changing a basic amino acid with a side-chain comprising a terminal amino (—NH2), with proved resistance to the treatment with some moAbs used in the cancer therapy. More particularly, this association is seen when these basic amino acids change to certain polar amino acids selected from cysteine and threonine.

Besides, changes of amino acids within the above-mentioned SEQ ID NO: 12 being said amino acids polar or neutral and substituted by bulky amino acids, being charged or neutral, are also associated with proved resistance to the treatment with some moAbs used in the cancer therapy. This is the case, for example, of mutation S464L and of mutation G465R.

Particular mutations R451C and K467T are detected in a mutated protein comprising the peptide sequence defined in SEQ ID NO: 1.

Besides, the above-indicated mutations and mutations S464L and G465R are detected in a mutated protein comprising the peptide sequence defined in SEQ ID NO: 13.

These markers may then be used to track the evolution of the acquired resistance mechanisms to anti-EGFR therapies. Detection of acquired resistance may be a useful tool for proposing another therapeutic approach or medical regimen along the follow-up of the disease evolution.

Thus, in a first aspect the invention relates to a peptide sequence with a length from 17 to 100 amino acids and comprising the sequence SEQ ID NO: 13
$X^1$SLKEISDGDVIIX$^4$X$^5$NX$^2$, wherein
$X^1$ is selected from R and C;
$X^4$ is selected from S and L;
$X^5$ is selected from G and R;
$X^2$ is selected from K and T; and wherein at least one of $X^1$, $X^4$, $X^5$ and $X^2$ is, respectively, C, L, R or T.

SEQ ID NO: 13 encompasses any of the above-defined mutations, but at least one of them: R451C, S464L, G465R or K467T.

In a particular embodiment, the invention relates to a peptide sequence with a length from 17 to 100 amino acids and comprising the sequence SEQ ID NO: 1
$X^1$SLKEISDGDVIISGNX$^2$, wherein:
$X^1$ is selected from R and C;
$X^2$ is selected from K and T; and
wherein if $X^1$ is C, then $X^2$ is selected independently from K and T, and
if $X^1$ is R, then $X^2$ is T.

SEQ ID NO: 1 encompasses any of the above-defined mutations, but at least one of them: R451C or K467T. In other words, $X^1$ and $X^2$ have the indicated meaning but with the proviso that at least one of $X^1$ or $X^2$ are, respectively, the mutated forms C or T; or both $X^1$ and $X^2$ are the mutated forms C and T.

This SEQ ID NO: 1 derives from human EGFR protein of SEQ ID NO: 2. Thus, it is a fragment of the human protein sequence, said fragment including at least one of the indicated mutations. Therefore, the resting of the amino acids up to 100 are the ones located in the protein sequence of SEQ ID NO: 2, being either flanking said SEQ ID NO: 1 or a sequence linked to the C-terminal end of SEQ ID NO: 1 and defined by the amino acid $X^2$.

Advantageously, these mutations (R451C, S464L, G465R or K467T) represent alternatives that can be tested in a sample of a subject suspected of having acquired resistance or a primary resistance to the anti-EGFR moAb therapies. Thus, besides other mutations that may be present or not in the sample of a subject, the mutations proposed in SEQ ID NO: 1 (R451C or K467T) or even in SEQ ID NO: 13 (R451C, S464L, G465R or K467T) serve to detect possible resistant subjects not detectable by other means. In particular, mutations R451C and K467T imply the additional advantage of indicating that some anti-EGFR moAb therapies are still permissive (or efficient). In particular, mutations R451C and K467T are permissive to panitumumab. This means that, if at least one of these two mutations are detected, at least panitumumab treatment may be recommended.

In a second aspect, the invention relates to an oligonucleotide comprising a sequence coding for SEQ ID NO: 1 or SEQ ID NO: 13.

The isolated peptide comprising SEQ ID NO: 1 or SEQ ID NO: 13 is the key product leading to the detection of mutated forms of EGFR protein of great interest in the field of cancer therapy. These mutated forms of the protein are also detectable in the form of an oligonucleotide comprising a sequence coding for SEQ ID NO: 1 or for SEQ ID NO: 13.

Oligonucleotides coding for SEQ ID NO: 1 or for SEQ ID NO: 13 are those including the nucleotide changes that lead to at least one of the above mentioned amino acid changes taking into account the codon degeneracy (redundancy of the genetic code) in these mutation positions. These oligonucleotides may be used then as hybridization probes for detecting the particular mutations that lead to the amino acid changes.

In addition, all these oligonucleotides are suitable probes allowing detecting the presence or not of the nucleotide mutations leading to amino acid changes in a peptide sequence comprising SEQ ID NO: 1 or SEQ ID NO: 13.

In particular, the invention is based on the surprising identification of the amino acid substitutions of an arginine by a cysteine at position 451 of the EGFR protein; of a serine by a leucine at position 464 of the EGFR; of a glycine by an arginine at position 465; and of a lysine by a threonine at position 467 of the EGFR protein.

The amino acid change K467T is the result of the nucleotide change A→C at nucleotide 1400 (also known herein as A1400C) of the mRNA variant 1 of the EGFR gene (Codon AAA is changed to ACA). The amino acid change R451C is the result of the nucleotide change C→T at nucleotide 1351 (also known herein as C1351T) of the mRNA variant 1 of the EGFR gene (Codon CGC is changed to TGC). The amino acid change S464L is the result of the nucleotide change C→T at nucleotide 1391 (also known herein as C1391T) of the mRNA variant 1 of the EGFR gene (Codon TCA is changed to TTA). The amino acid change G465R is the result of the nucleotide change G→A at nucleotide 1393 (also known herein as G1393A) of the mRNA variant 1 of the EGFR gene (Codon GGA is changed to AGA).

All these amino acid changes may be the result of other mutations in the codon coding for them. In particular, all those nucleotide changes leading to a cysteine at position 451 of SEQ ID NO: 2 (human EGFR protein), to a leucine at position 464 of SEQ ID NO: 2, to an arginine at position 465 of SEQ ID NO: 2; and to a threonine at position 467 of SEQ ID NO: 2.

As already indicated above, each of the above nucleotide changes refers to the mRNA, transcript variant 1 sequence of the EGFR gene (also known as ERBB1, PIG61, proto-oncogene c-ErbB-1, avian erythroblastic leukemia viral (v-erb-b) oncogene homolog receptor tyrosine-protein kinase erbB-1, or HER1). The sequence of the mRNA, transcript variant 1, of the EGFR gene is that corresponding to SEQ ID NO: 3 (or GenBank accession number NM_005228.3, version 3 of sequence and database release available on May 18, 2014) as well as any variant thereof, wherein said variant codes for the EGFR protein. The EGFR protein corresponds to SEQ ID NO: 2 (GenBank accession number NP_005219.2 version 2 of sequence and database release of May 18, 2014) or any variant thereof that maintains the basic structure of the EGFR protein. SEQ ID NOs: 2 and 3 are from human (Homo sapiens). Nonetheless, EGFR is highly conserved in most of the mammals and the herewith mutation points comprise in the wild-type sequences the same amino acids in most of mammals. Therefore, the invention encompasses the same mutations but determined in a sequence of EGFR protein or gene of any mammal.

Another aspect of the invention is a set of primers consisting of SEQ ID Nos: 6 (CAAAGTTTTCAGGGATACATTGTTTTT) and 7 (TTAAATGGGAATAGCCCTTCAATATT).

This set of primers allows amplifying the genomic region comprising the portion of the EGFR coding region wherein the nucleotide changes resulting in the mutations of the present invention are located. They are thus related with the novel amino acidic mutations identified by the inventors, and they allow amplifying the EGFR coding region coding for the fragment herewith named SEQ ID NO: 12 (LRSLKEISDGDVIISGNKNLC) that has been surprisingly found as a key region including many mutations leading to resistance (acquired or primary) to treatment with anti-EGFR moAbs. Particularly, the set of primers consisting of SEQ ID NO: 6 and 7 allow amplification of EGFR coding region leading to Exon 12 in the variant 1 of mRNA transcript. This set allows determining if mutations R451C, S464L, G465R and K467T are present in the final resulting EGFR protein. More in particular if mutations R451C and K467T are present in the final resulting EGFR protein.

Another aspect of the invention is a kit that comprises a set of primers consisting of: the set of primers of SEQ ID NOs: 6 and 7, and/or an oligonucleotide as defined in the second aspect of the invention.

This kit is a usable tool to detect the presence of the mutations (R451C, S464L, G465R and K467T) of SEQ ID NO: 13, and more particularly of mutations R451C and K467T of SEQ ID NOs: 1, or of any amino acid sequence comprising it, in an easy and fast way, since it includes the primers for amplifying regions of EGFR gene that may include the disclosed mutations correlated with resistance to cetuximab treatment.

Also another aspect of the invention is, therefore, the kit as defined above, for use in the prediction of the response of a subject to a therapy regimen comprising anti-EGFR monoclonal antibodies. Or the use of a kit as defined above for predicting response of a subject to a therapy regimen comprising anti-EGFR monoclonal antibodies.

Further, the invention also relates to an in vitro method of predicting the response of a subject therapy regimen comprising cetuximab and/or panitumumab, wherein the method comprises:

(i) determining in a sample taken from the subject and by means selected from the group consisting of genotype methods, and/or protein sequencing methods if mutations are present or absent in a fragment defined by SEQ ID NO: 12, which is a fragment from amino acid 450 to amino acid 470 of the consensus wild-type amino acid sequence of human EGFR of SEQ ID NO: 2;

and ii) correlating the presence of any mutation identified in step i) with resistance of the subject to the therapy regimen comprising cetuximab, or correlating the absence of mutations in step i) with response of the subject to therapy regimen comprising panitumumab.

Thus, SEQ ID NO: 12 corresponds to the wild-type amino acid fragment (or sequence) of the human EGFR, and mutations in relation to this consensus wild-type amino acid sequence are determined within this SEQ ID NO: 12, that has been discovered as a meaningful fragment of EGFR regarding prediction of anti-EGFR moAb treatments. This SEQ ID NO: 12 forms also part of the invention (LRSLKEISDGDVIISGNKNLC) as an isolated peptide.

The invention also relates to in vitro methods of predicting the response of a subject therapy regimen comprising cetuximab and/or panitumumab, wherein the method comprises:

i) determining by means selected from the group consisting of genotype methods, and/or protein sequencing methods, the presence or absence of at least one of the following amino acids:

a cysteine at position 451 of the amino acid sequence corresponding to SEQ ID NO: 2, a leucine at position 464 of the amino acid sequence corresponding SEQ ID NO: 2, an arginine at position 465 of the amino acid sequence corresponding SEQ ID NO: 2; and a threonine at position 467 of the amino acid sequence corresponding to SEQ ID NO: 2, in a sample taken from the subject; and ii) correlating the presence of any of the amino acids identified in step i) with resistance of the subject to the therapy regimen comprising cetuximab, or correlating the absence of all of these amino acids in step i) with response of the subject to therapy regimen comprising panitumumab.

Further, the invention also relates, in a particular embodiment, to an in vitro method of predicting the response of a subject therapy regimen comprising cetuximab and/or panitumumab, wherein the method comprises:

i) determining by means selected from the group consisting of genotype methods, and/or protein sequencing methods, the presence or absence of at least one of the following amino acids:

a cysteine at position 451 of the amino acid sequence corresponding to SEQ ID NO: 2, and a threonine at position 467 of the amino acid sequence corresponding to SEQ ID NO: 2, in a sample taken from the subject; and ii) correlating the presence of any of the amino acids identified in step i) with resistance of the subject to the therapy regimen comprising cetuximab, or correlating the absence of all of these amino acids in step i) with response of the subject to therapy regimen comprising panitumumab.

This in vitro method encompasses detecting if in exon 12 of the mRNA variant 1 of the human EGFR gene finally coding for EGFR protein of SEQ ID NO: 2 there is a nucleotide change leading to a change of an amino acid with a side-chain comprising a terminal amino (—NH2) in the wild-type gene for a polar amino acid, whose carbohydrate side-chain comprises radicals with atoms from the oxygen group.

The put into practice of the in vitro method of predicting the response of a subject to a therapy regimen comprising cetuximab and/or panitumumab, implies the advantage of accommodating the more suitable therapy for the subject, and avoids wrong or not useful enough therapeutically approaches incurring waste time, which is an essential aspect for the subject and the success of the treatment, especially if the subject is affected with cancer.

In addition, detection of any of these mutations allows determining if a secondary resistance to cetuximab treatment has been developed in the subject, said subject not initially carrying the mutations in the EGFR gene.

Thus, another aspect of the invention is an in vitro method for determining the acquired resistance to a therapy regimen comprising cetuximab, the method comprising:

i) determining by means selected from the group consisting of genotype methods, and/or protein sequencing methods, the presence or absence of at least one of the following amino acids:

a cysteine at position 451 of the amino acid sequence corresponding to SEQ ID NO: 2, a leucine at position 464 of the amino acid sequence corresponding to SEQ ID NO: 2, an arginine at position 465 of the amino acid sequence corresponding to SEQ ID NO: 2, and a threonine at position 467 of the amino acid sequence corresponding to SEQ ID NO: 2, in a sample taken from the subject; and ii) correlating the presence of any of the amino acids identified in step i) with acquired resistance of the subject to the therapy regimen comprising cetuximab, or correlating the absence of all of these amino acids in step i) with response of the subject to therapy regimen comprising panitumumab.

This in vitro method for determining the acquired resistance in a subject after treatment with cetuximab, advantageously allows stopping the treatment and further to avoid secondary or accompanying cetuximab adverse effects.

Moreover, other approaches can be taken as fast as possible.

As above, this in vitro method for determining the acquired resistance encompasses detecting if in exon 12 of the mRNA variant 1 of the human EGFR gene finally coding for EGFR protein of SEQ ID NO: 2 there is a nucleotide change leading to a change of an amino acid with a side-chain comprising a terminal amino (—NH2) in the wild-type gene for a polar amino acid, whose carbohydrate side-chain comprises radicals with atoms from the oxygen group. This in vitro method encompasses also detecting if at least in exon 12 of the mRNA variant 1 of the human EGFR gene finally coding for EGFR protein fragment of SEQ ID NO: 12, there is a nucleotide change leading to a change of wild-type amino acids to bulky amino acids (i.e. those with a side-chain consisting of branched or unbranched C1-C4 hydrocarbons, optionally with a terminal amino group) and/or to polar or charged amino acids. Wild-type amino acid refers to the amino acid according to the consensus amino acid sequence of human EGFR protein (SEQ ID NO: 2).

Another aspect of the invention is an in vitro method of identifying, in a sample taken from a subject, the presence or absence of a cysteine at position 451 of the amino acid sequence corresponding to SEQ ID NO: 2; and/or the presence or absence of a leucine at position 464 of the amino acid sequence corresponding to SEQ ID NO: 2; and/or the presence or absence of an arginine at position 465 of the amino acid sequence corresponding to SEQ ID NO: 2; and/or the presence or absence of a threonine at position 467 of the amino acid sequence corresponding to SEQ ID NO: 2, the method comprising determining the sequence of SEQ ID NO: 2, at least from position 450 to position 470.

This later aspect can also be formulated as an in vitro method of identifying, in a sample taken from a subject, the presence or absence of a cysteine at position 451 of the amino acid sequence corresponding to SEQ ID NO: 2; and/or the presence or absence of a leucine at position 464 of the amino acid sequence corresponding to SEQ ID NO: 2; and/or the presence or absence of an arginine at position 465 of the amino acid sequence corresponding to SEQ ID NO: 2; and/or the presence or absence of a threonine at position 467 of the amino acid sequence corresponding to SEQ ID NO: 2, the method comprising determining the amino acid at positions 451 and/or 464 and/or 465 and/or 467 by means selected from the group consisting of genotype methods, and/or protein sequencing methods.

DETAILED DESCRIPTION OF THE INVENTION

Figure 1:
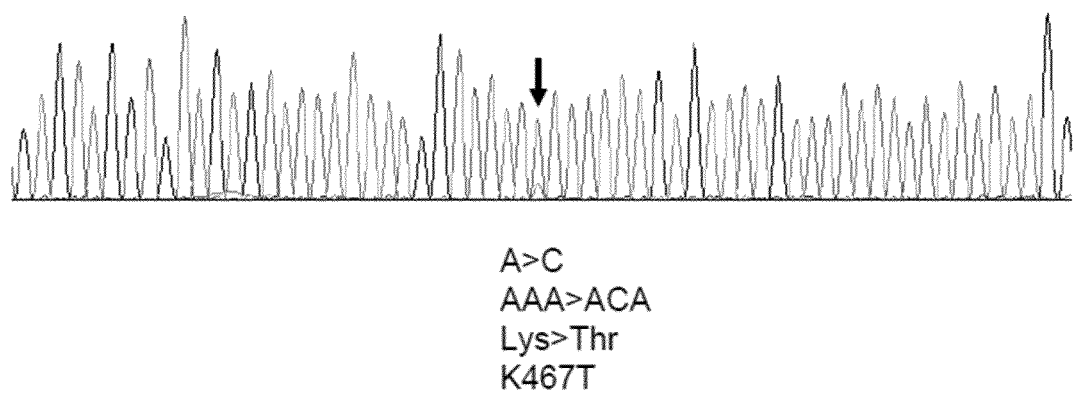
FIG. 1 is the plot of two displays of sequencing results obtained by conventional Sanger sequencing (plot A) and Next Generation Sequencing (NGS) in a 454 GS Junior platform (Roche Applied Science, Mannheim, Germany) (plot B). It shows the acquisition of mutations in the EGFR ectodomain following treatment with cetuximab in two samples. (A) In patient #31, the post-treatment tumor sample had acquired an A→C substitution at nucleotide 1400 of EGFR gene that was not present in a pre-treatment biopsy, causing a substitution of a lysine to a threonine at amino acid 467 (K467T). (B) In patient #35, a C→T substitution at nucleotide 1351 of the EGFR gene was detected in the post-treatment sample, leading to a substitution of an arginine to a cysteine at amino acid 451 (R451C).
Figure 1:
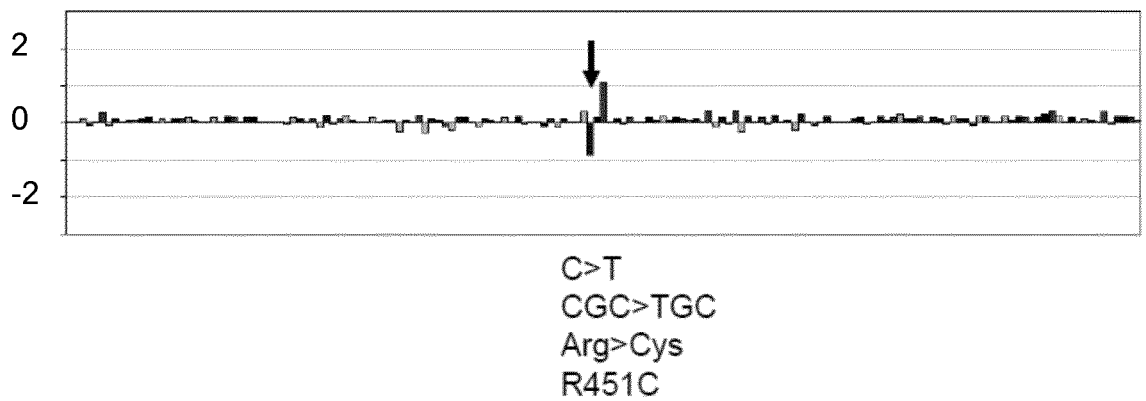

In general, the following words or phrases have the indicated definition when used in the description, examples and claims.

The term "therapy regimen" as used in the state of the art and also herein refers to any therapy intended to prevent, slow, arrest or reverse the growth of a precancerous lesion, cancer or a cancer metastasis. It includes chemotherapy, radiation therapy, immunotherapy, monoclonal antibody therapy or other methods.

By "response" is to be understood any kind of improvement either clinical or non-clinical selected from, but not limited to, measurable reduction in tumour size or evidence of disease or disease progression, stable disease, increase or elongation of progression of free survival or reduction in toxicity.

"Progression free survival" indicates the length of time during and after treatment that the cancer does not grow. Progression free survival includes the amount of time patients have experienced a complete response or partial response, as well as the amount of time patients have experienced stable disease.

"A complete response" to a therapy defines patients with valuable but non-measurable disease, whose tumour and all evidence of disease disappeared.

"A partial response" to a therapy defines patients with anything less than complete response.

"An anti-EGFR monoclonal antibody (anti-EGFR moAb)" relates to a monoclonal antibody and to a fragment thereof that are able to recognize epitopes in the EGFR sequence protein. Approved moAb which recognize different epitopes of EGFR are cetuximab and panitumumab, but other moAb could be used in the therapy regimen for facing cancer disclosed in the present invention. Suitable antibody fragments include F(ab), F(ab'), Fv and nanobodies, among others.

The expression "genotype methods" includes all those methodologies and processes suitable for determining the genotype or, which is the same for identifying the nucleotide in a given position. Examples of said methodologies encompass Sanger sequencing, pyrosequencing, allele-specific PCR, denaturing high pressure liquid chromatography (DHPLC), Allele Specific Primer Extension (ASPE), DNA biochips/microarrays and dynamic allele-specific hybridization (DASH).

For "protein sequencing methods" is to be understood any technique allowing to determine the amino acid sequence of a protein, as well as which conformation the protein adopts and the extent to which it is complexed with any non-peptide molecules. The determination of amino acid composition may be performed by hydrolysis or separation of the amino acids. Known technologies include the Sanger sequencing, Edman degradation and mass spectrometry.

If not indicated to the contrary, all sequences relating EGFR gene, mRNA variant and EGFR protein relate to the human one with the database accession numbers listed along the description. Also if not indicated to the contrary, oligonucleotide sequences are shown in the 5'-3' direction, and peptide sequences are shown starting from the N-terminus amino acid ((also known as the amino-terminus, NH2-terminus, N-terminal end or amine-terminus) of the peptide, according to the convention for writing peptide sequences.

All the amino acid sequences, as well as of oligonucleotides may be synthesized following appropriate peptide or oligonucleotide chemical synthesis. Examples of peptide synthesis include solid-phase synthesis and liquid-phase synthesis, both processes coupling the carboxyl group or C-terminus of one amino acid to the amino group or N-terminus of another. Unintended reactions are avoided in solid-phase synthesis using protecting groups, such as 9-fluorenylmethyloxycarbonyl (Fmoc) and Tert-butyloxycarbonyl (t-Boc). Alternatively, the peptides may be obtained by DNA recombinant technologies. Oligonucleotides may be obtained by solid-phase synthesis using phosphoramidite method and phosphoramidite building blocks derived from protected 2'-deoxynucleosides (dA, dC, dG, and T), ribonucleosides (A, C, G, and U), or chemically modified nucleosides. Oligonucleotides may also be derived from DNA digestion with appropriate restriction enzymes.

As already explained above, prior art teachings show that mutations at domain III of EGFR may help to map critical points for the interaction of moAbs (cetuximab and/or panitumumab). Nonetheless, these data may serve to detect specific epitopes but they are not concluding in terms of resistance to treatment, since only specific amino acid exchanges encompass this information (that of resistance, either primary or secondary resistance). Particularly, acquired resistance to treatment is of great importance in order to modify the therapeutically approaches and avoid wasting time and efforts.

The present invention is based on novel mutations in the coding region of the EGFR gene. The novel mutations of the present invention are useful to predict the response to moAb-based therapy of a patient with mCRC. In particular, they are useful to predict primary resistance and the appearance of a secondary resistance.

As already indicated above, each of the disclosed nucleotide changes lead to the substitution to a cysteine at position 451 of SEQ ID NO: 2 (human EGFR protein), to a leucine at position 464 of SEQ ID NO: 2, to an arginine at position 465 of SEQ ID NO: 2, and to a threonine at position 467 of SEQ ID NO: 2. All these particular mutations are located in a fragment from amino acid 450 to amino acid 470 of this SEQ ID NO: 2, said fragment herewith named SEQ ID NO: 12.

The peptide according to the invention, with a length from 17 to 100 amino acids and comprising the sequence SEQ ID NO: 1 includes any of the mutations R451C or K467T.

In a particular embodiment, this peptide is selected from the group consisting of: a sequence comprising SEQ ID NO: 1 wherein $X^1$ is R and $X^2$ is T; a sequence comprising SEQ ID NO: 1 wherein $X^1$ is C and $X^2$ is T; and a sequence comprising SEQ ID NO: 1 wherein $X^1$ is C and $X^2$ is K.

In a more particular embodiment, the peptide consists in SEQ ID NO: 1 and, more particularly that SEQ ID NO: 1 selected from the group consisting of SEQ ID NO: 1 wherein $X^1$ is R and $X^2$ is T; SEQ ID NO: 1 wherein $X^1$ is C and $X^2$ is T; and SEQ ID NO: 1 wherein $X^1$ is C and $X^2$ is K. These sequences are represented by SEQ ID NO: 8 (RSLKEISDGDVIISGNT), SEQ ID NO: 9 (CSLKEISDGDVIISGNT) and SEQ ID NO: 10 (CSLKEISDGDVIISGNK).

In a particular embodiment, the peptide with a length from 17 to 100 amino acids and comprising the sequence SEQ ID NO: 1, further comprises SEQ ID NO: 4 NLCYANTINWKKLFGTSGGKTKIIX$^3$, wherein $X^3$ is selected from S and R.

The peptide comprising both SEQ ID NO: 1 and SEQ ID NO: 4 corresponds, in a particular embodiment, to a continuous amino acid sequence starting with SEQ ID NO: 1. This sequence has 42 amino acids and corresponds to a fragment of EGFR protein coded partially by exon 12 of the EGFR gene. It is represented by, or consists in SEQ ID NO: 5 ($X^1$SLKEISDGDVIISGNX$^2$NLCYANTINWKK-LFGTSGGKTKIIX$^3$)

In another particular embodiment, the peptide with a length from 17 to 100 amino acids and comprising the sequence SEQ ID NO: 13, further comprises SEQ ID NO: 4. This peptide comprising both SEQ ID NO: 13 and SEQ ID NO: 4 corresponds, in a particular embodiment, to a continuous amino acid sequence starting with SEQ ID NO: 13. It has 42 amino acids and corresponds to a fragment of EGFR protein coded partially by exon 12 of the EGFR gene. It is represented by, or consists in SEQ ID NO: 14 ($X^1$SLKEISDGDVIIX$^4$X$^5$NX$^2$NLCYANTINWKK-LFGTSGGKTKIIX$^3$)

Indeed, this SEQ ID NO: 5 includes any or all of the mutations R451C and K467T, and further it encompasses the option of including mutation S492R. Thus, $X^1$, $X^2$ and $X^3$ have the same meaning as indicated above; and if $X^1$ is C, then $X^2$ is selected independently from K and T, and if $X^1$ is R, then $X^2$ is T.

Mutation S492R was firstly disclosed by the inventors in Montagut et al., (supra) as a key mutation for determining also resistance to moAb in cancers, including metastasic colorectal cancer.

Besides, SEQ ID NO: 14 includes any or all of the mutations R451C, S464L, G465R and K467T, and further it encompasses the option of including mutation S492R. Thus, $X^1$, $X^2$, $X^3$, $X^4$ and $X^5$ have the same meaning as indicated above, but at least one of $X^1$, $X^2$, $X^4$ or $X^5$ is, respectively, C, L, R or T.

In another particular embodiment, the peptide sequence comprising SEQ ID NO: 1 or SEQ ID NO: 13 has a length from 17 to 50 amino acids. In another particular embodiment it has a length from 17 to 25 amino acids (that is 17, 18, 19, 20, 21, 22, 23, 24 or 25). In another most particular embodiment the peptide sequence has a length of 17 amino acids. In another particular embodiment it has a length of 21 amino acids, being any of SEQ ID NO: 1 or SEQ ID NO: 13 flanked in the N-terminal end by a leucine (L) and in the C-terminal end by the tripeptide N-Asparagine-Leucine-Cysteine-C (abbreviated NLC)

In addition, and as will be depicted in the examples below, the inventors also detected a new mutation leading to resistance to moAb in cancers, including metastasic colorectal cancer, namely a change of an isoleucine by a methionine at position 491 of SEQ ID NO: 2 (human EGFR protein). This mutation is herewith named I491M. The amino acid change I491M is the result of the nucleotide change A→G at nucleotide 1473 (also known herein as A1473G) of the mRNA variant 1 of the EGFR gene (Codon ATA is changed to ATG)

New mutations identified in the present invention are alternatives, but may also be used in combination to assure a proper therapy selection.

The invention encompasses oligonucleotides coding for SEQ ID NO: 1 or SEQ ID NO: 13. In the particular embodiment of an oligonucleotide coding for SEQ ID NO: 1 or SEQ ID NO: 13, optionally in combination with any embodiment above or below, said oligonucleotide further codes for SEQ ID NO: 4 and thus in another particular embodiment the oligonucleotide codes for SEQ ID NO: 5 or for SEQ ID NO: 14. Particular oligonucleotides are those consisting in nucleotide sequences coding for any of sequences SEQ ID NO: 8 to 10. These oligonucleotides, as above exposed, may be used as hybridization probes for detecting the mutations.

The kit according to the invention comprises, besides the set of primers disclosed above, oligonucleotide probes for detecting wild-type or mutated forms of EGFR gene coding for any of the mutations R451C and K467T. Examples of these probes for detecting mutated forms of EGFR gene, consists in oligonucleotides selected from those coding for any of SEQ ID NO: 1, 5, 8, 9 and 10.

The probes consisting in the oligonucleotides selected from those coding for any of SEQ ID NO: 1, 5, 8, 9 and 10 are nucleotide sequences comprising the several options of codon degeneracy in the corresponding mutation points.

Particular probes for the detection of the mutation R451C are those complementary to the mutated region of the EGFR, wherein the nucleotide changes resulting in the mutation R451C of the present invention is located, being either the coding or complementary region of the gene. Thus, they hybridize with a fragment of the nucleotide sequence carrying the mutation, and allows detecting the nucleotide change C→T at position 1351 disclosed above.

Particular probes for the detection of the mutation K467T are those complementary to the mutated region of the EGFR wherein the nucleotide changes resulting in the mutation K467T of the present invention is located, being either the coding or complementary region of the gene. Thus, it hybridizes with a fragment of the nucleotide sequence carrying the mutation, and allows detecting the nucleotide change A→C at position 1400 disclosed above.

Other particular oligonucleotide probes in the kit are for detecting wild-type or mutated forms of EGFR gene coding for any of the mutations S464L and G465R.

Particular probes for the detection of the mutation S464L are those complementary to the mutated region of the EGFR, wherein the nucleotide changes resulting in the mutation S464L of the present invention is located, being either the coding or complementary region of the gene. Thus, they hybridize with a fragment of the nucleotide sequence carrying the mutation, and allows detecting the nucleotide change C→T at position 1391 disclosed above.

Other particular probes for the detection of the mutation G465R are those complementary to the mutated region of the EGFR, wherein the nucleotide changes resulting in the mutation G465R of the present invention is located, being either the coding or complementary region of the gene. Thus, they hybridize with a fragment of the nucleotide sequence carrying the mutation, and allows detecting the nucleotide change G→A at position 1393 disclosed above.

For "nucleotide sequence carrying the mutation" is to be understood any of the coding or complementary DNA chains in the DNA genomic structure, as well as an mRNA chain which is going to be translated.

The kits of the invention may, optionally in combination with any embodiment above or below, further comprise additional reagents for detecting mutations in the KRAS and/or PIK3CA, and/or BRAF genes, and/or additional mutations in EGFR gene. These reagents include specific primers for detecting particular mutations in all these genes, and particularly mutations associated with resistance to a therapy regimen comprising cetuximab and/or panitumumab.

Other reagents included in the kit relate to oligonucleotide probes that can hybridize either with the wild-type or mutated forms of all these genes.

Thus, in a particular embodiment, optionally in combination with any of the embodiments above or below, the kit comprises tools and means (reagents) to detect the mutations in KRAS selected from the group consisting of G12A; G12C; G12D; G12R; G12S; G12V; G13A; G13C, G13D; G13V as defined by Karapetis et al., "K-ras Mutations and Benefit from Cetuximab in Advanced Colorectal Cancer", The New England Journal of Medicine—2008, Vol. 359, pp.: 1757-1765. All these mutations are placed on codons 12 and 13 of the protein sequence of K-ras identified with the GenBank accession number NP_004976.2 from Jul. 24, 2011 (named GTPase KRas isoform b precursor) and NP_203524.1 from Jul. 24, 2011 (named GTPase KRas isoform a precursor. In another preferred embodiment the kit comprises reagents to detect mutations in exons 9 and 20 of the PIK3CA gene that codifies for the PIK3CA protein with the GenBank accession number NP_006209.2 from Jul. 17, 2011; and/or the V600E mutation placed on codon 600 of the protein sequence of BRAF identified with the GenBank accession number NP_004324.2 from Jul. 24, 2011. In another preferred embodiment the kit comprises means (reagents) to detect mutation S492R in EGFR protein of SEQ ID NO: 2. In another preferred embodiment the kit comprises means (reagents) to detect mutation I491M in EGFR protein of SEQ ID NO: 2.

The kits of the invention are in particular for use in the prediction of the response of a subject to a therapy regimen comprising anti-EGFR monoclonal antibodies, in particular cetuximab and/or panitumumab. More particularly, the subject is affected with cancer, and the cancer is metastatic colorectal cancer.

The invention relates according to one aspect of the invention to an in vitro method of predicting the response of a subject therapy regimen comprising cetuximab and/or panitumumab, wherein the method comprises:

(i) determining in a sample taken from the subject and by means selected from the group consisting of genotype methods, and/or protein sequencing methods if mutations are present or absent in a fragment defined by SEQ ID NO: 12, which is a fragment from amino acid 450 to amino acid 470 of the consensus wild-type amino acid sequence of human EGFR of SEQ ID NO: 2;

and ii) correlating the presence of any mutation identified in step i) with resistance of the subject to the therapy regimen comprising cetuximab, or correlating the absence of mutations in step i) with response of the subject to therapy regimen comprising panitumumab.

In a particular embodiment of the in vitro method in step (i) there are determined within the SEQ ID NO: 12 if at least one of the following mutations are present or absent: a change of an arginine by a cysteine at corresponding position 451 of the SEQ ID NO:2; a serine by a leucine at corresponding position 464 of the SEQ ID NO: 2; a glycine by an arginine at the corresponding position 465 of the SEQ ID NO: 2; and of a lysine by a threonine at the corresponding position 467 of the SEQ ID NO: 2.

In another particular embodiment, the in vitro method of predicting the response of a subject therapy regimen comprising cetuximab and/or panitumumab comprises:

i) determining by means selected from the group consisting of genotype methods, and/or protein sequencing methods the presence or absence of at least one of the following amino acids:

a cysteine at position 451 of the amino acid sequence corresponding to SEQ ID NO: 2, and a threonine at position 467 of the amino acid sequence corresponding to SEQ ID NO: 2, in a sample taken from the subject; and ii) correlating the presence of any of the amino acids identified in step i) with resistance of the subject to the therapy regimen comprising cetuximab, or correlating the absence of all of these amino acids in step i) with response of the subject to therapy regimen comprising panitumumab.

This particular embodiment encompasses determining if SEQ ID NO: 1 is present in the sample of the subject, and further correlating in step ii) the presence of any of the mutations R451C and/or K467T with resistance of the subject to the therapy regimen comprising cetuximab, or correlating the absence of all of these amino acids in step i) with response of the subject to therapy regimen comprising panitumumab.

In a more particular embodiment of the method, optionally in combination with any embodiments above or below step i) encompasses determining if additionally SEQ ID NO: 4 is present in the sample of the subject. Thus, after determining if any of the mutations R451C and/or S464L and/or G465R and/or K467T is present, the method includes also determining if mutation S492R is present in EGFR protein.

Detection of mutation S492R relates to the particular embodiment of the in vitro method, optionally in combination with any of the embodiments below or above, wherein step i) further comprises determining the presence or absence of an arginine at position 492 of the amino acid sequence corresponding to SEQ ID NO: 2, and wherein in step ii) the additional presence of the arginine identified in step i) is correlated with resistance of the subject to the therapy regimen comprising cetuximab.

In another particular embodiment, optionally in combination with any embodiments above or below, the in vitro method of predicting the response of a subject therapy regimen comprising cetuximab and/or panitumumab, further comprises determining in step (i) the presence or absence of a methionine at position 491 of the amino acid sequence corresponding to SEQ ID NO: 2, and wherein in step ii) the additional presence of the methionine identified in step i) is correlated with resistance of the subject to the therapy regimen comprising cetuximab.

In another particular embodiment, optionally in combination with any of the embodiments above or below, step i) is performed with a set of primers consisting of SEQ ID NOs: 6 and 7.

Further to the amplification with the above mentioned primers, in a particular embodiment step i) is performed by genotype methods. In another most particular embodiment, optionally in combination with any embodiment above or below, said genotype method is selected from Sanger sequencing, pyrosequencing, droplet digital PCR (ddPCR), allele-specific PCR, denaturing high pressure liquid chromatography (DHPLC), Allele Specific Primer Extension (ASPE), DNA biochips/microarrays and dynamic allele-specific hybridization (DASH). In even a most particular embodiment, the genotype method is pyrosequencing.

Examples of pyrosequencing genotype methods include, among others, the next generation sequencing (NGS) methods known as 454 High though output pyrosequencing, sequencing by synthesis (Illumina), and Chain termination sequencing (Sanger sequencing).

Alternatively, step i) includes specific probes to detect wild-type or mutated points as genotyping method of the amplified regions. Particular probes are those oligonucleotides coding for SEQ ID NO: 1, SEQ ID NO: 5, SEQ ID NO: 8, SEQ ID NO: 9, and SEQ ID NO: 10. All these oligonucleotides are complementary to nucleotide sequences of mutated EGFR gene.

The in vitro method for predicting the response of a subject to a therapy regimen comprising cetuximab and/or panitumumab, is carried out in a sample comprising the tumour, in which the nucleotide changes in the EGFR gene of the present invention can be detected. In cases of mCRC, the sample can be used directly as obtained from the source or following a pre-treatment of the sample. The sample may additionally comprise normal tissue adjacent to said tumour. Accordingly, in case of mCRC the sample is selected from a primary colorectal cancer biopsy or a biopsy of a metastasis thereof. In other words, the sample may be a biopsy from colorectal cancer samples, including primary tumors and metastases. In a preferred embodiment, the metastasis is in the liver tissue.

Patients comprising any of the new identified mutations are likely to show response to a therapy regimen not comprising cetuximab as measured by any suitable clinical or sub-clinical increase or elongation in progression free survival.

In a preferred embodiment the therapy regimen is cetuximab alone or in combination with a chemotherapy regimen based on irinotecan, oxaliplatin and/or 5-fluorouracil (5-FU or 5FU). In a preferred embodiment the therapy regimen is panitumumab alone or in combination with a chemotherapy regimen based on irinotecan, oxaliplatin and/or 5-fluorouracil.

The invention further provides also methods for deciding and/or recommending a therapy regimen for subjects affected with cancer, preferably mCRC, comprising: i) determining by means selected from the group consisting of genotype methods, and/or protein sequencing methods the presence or absence of at least one of the following amino acids: a cysteine at position 451 of the amino acid sequence corresponding to SEQ ID NO: 2, and a threonine at position 467 of the amino acid sequence corresponding to SEQ ID NO: 2, in a sample taken from the subject; and ii) recommending the administration to said subject of an effective amount of cetuximab, or a composition thereof, if all the mutations are absent, or panitumumab, or a composition thereof, if at least one of the mutations is present.

The invention encompasses also an in vitro method for determining the acquired resistance to a therapy regimen comprising cetuximab, the method comprising, in a particular embodiment of this aspect:

i) determining by means selected from the group consisting of genotype methods, and/or protein sequencing methods, the presence or absence of at least one of the following amino acids:

a cysteine at position 451 of the amino acid sequence corresponding to SEQ ID NO: 2, and a threonine at position 467 of the amino acid sequence corresponding to SEQ ID NO: 2, in a sample taken from the subject; and ii) correlating the presence of any of the amino acids identified in step i) with acquired resistance of the subject to the therapy regimen comprising cetuximab, or correlating the absence of all of these amino acids in step i) with response of the subject to therapy regimen comprising panitumumab.

As above exposed, the invention provides also an in vitro method of identifying, in a sample taken from a subject, the presence or absence of a cysteine at position 451 of the amino acid sequence corresponding to SEQ ID NO: 2; and/or the presence or absence of a threonine at position 467 of the amino acid sequence corresponding to SEQ ID NO: 2 by means selected from the group consisting of genotype methods, and/or protein sequencing methods. In a preferred embodiment the in vitro method of identifying the presence or absence of one or both of these mutations in SEQ ID NO: 2, further comprises identifying the presence or absence of an arginine at position 492 of SEQ ID NO: 2 by means selected from the group consisting of genotype methods, and/or protein sequencing methods.

In a particular embodiment, optionally in combination with any embodiment above or below, the method of identifying the presence or absence of a cysteine at position 451 of the amino acid sequence corresponding to SEQ ID NO: 2; and/or the presence or absence of a leucine at position 464 of the amino acid sequence corresponding to SEQ ID NO: 2; and/or the presence or absence of an arginine at position 465 of the amino acid sequence corresponding to SEQ ID NO: 2; and/or the presence or absence of a threonine at position 467 of the amino acid sequence corresponding to SEQ ID NO: 2, is carried out by determining the sequence of SEQ ID NO: 2 up to position 467 by means selected from the group consisting of genotype methods, and/or protein sequencing methods. In a preferred embodiment, the method is carried out by determining the sequence of SEQ ID NO: 2 from position 450 to 470 (SEQ ID NO: 12), and more preferably from 451 to position 467. For "determining a sequence up to a position" is to be understood that the sequencing is performed from oligonucleotide or amino acid from position 1 of said sequence to the position (nucleotide or amino acid) of interest (in this particular case, to amino acid 467 or to the nucleotide leading to this amino acid).

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Tumor Samples and Patients

There was performed a proof-of-concept approach to study and characterize the presence of heterogeneous mutations emerging after cetuximab-based therapy in routine clinical practice. All mCRC consenting patients treated with anti-EGFR moAb at Parc de Salut Mar Biobank (MARBiobanc, Barcelona, Spain) Hospital del Mar institution between January 2010 and June 2013 were included in this study. In 34 patients the specimens were prospectively collected for this study and in 3 patients there were analyzed sequential biopsies taken in the past in the context of their routine clinical management. In the analysis, there were only included patients that had good quality paired pre- and post-treatment biopsies and that had acquired resistance to anti-EGFR based-therapy defined as progression disease following a) complete response or partial response or b) stable disease for more than 16 weeks (7-9). Response was evaluated according to the Response Evaluation Criteria in Solid Tumors (RECIST)(Eisenhauer et al., "New response evaluation criteria in solid tumours: revised RECIST guideline (version 1.1)", Eur J Cancer 2009, Vol. 45(2):228-247). Tumoral biopsy obtained during the regular diagnosis procedure was used as the pre-treatment (initial) sample. In most cases this sample was obtained from the primary tumor during routine colonoscopy. A second initial biopsy from a metastatic site is not routine and was not performed unless necessary for pathologic diagnosis. The study included re-biopsy following treatment failure in patients that consented to this extra procedure. Re-biopsies at the time of progression were obtained from the most accessible lesion with less potential risk of related complications for the patient according to ethical considerations. Serum samples were collected before starting the cetuximab-based therapy and at the time of progression. When a mutation was detected in the post-treatment biopsy sample, the serum sample from that same patient was analyzed for that specific mutation. In this study, there are included nine cases (patients #21 to #28 and patient #36) that had been previously assessed for EGFR S492R, KRAS exon 2, BRAF V600E and PIK3CA mutations by direct sequencing and that in the current work were analyzed for the mutations reported above (R451C and K467T) using deep-sequencing technology. Biological samples were obtained from Parc de Salut Mar Biobank (MARBiobanc). This study was approved by the local Ethics Board (CEIC-2012/474111). All participating patients signed written informed consent.

For the KRAS, BRAF, NRAS, PIK3CA and EGFR sequencing, DNA extraction from tumoral samples was performed as previously described by Diaz et al. "The molecular evolution of acquired resistance to targeted EGFR blockade in colorectal cancers", Nature-2012, Vol No. 486, pp.:537-40. Mutational analysis of KRAS (exons 2, 3 and 4), BRAF (exon15), NRAS (exons 2 and 3), PIK3CA (exons 9 and 20) and EGFR (exon 12, 13) was performed by Sanger sequencing using BigDye v3.1 (Applied Biosystems, Foster City, Calif.) following the manufacturer's instructions and analyzed on a 3500Dx Genetic Analyzer (Applied Biosystems). All cases were also screened by pyrosequencing using a Next Generation Sequencing (NGS) 454 GS Junior platform (Roche Applied Science, Mannheim, Germany). Moreover, processed and quality-filtered reads were analyzed using the GS Amplicon Variant Analyzer software version 2.5p1 (Roche). Mutations detected by NGS were confirmed by competitive allele-specific TaqMan® PCR (CAST-PCR, Applied Biosystems) when specific assays were available.

Primers for EGFR sequences were those disclosed above and defined by the set of primers consisting in SEQ ID NOs: 6 and 7. The pair of SEQ ID NO: 6 and SEQ ID NO: 7 served for amplifying entirely exon 12 that could contain mutations R451C and K467T, and some intron flanking regions. This sequence is represented by SEQ ID NO: 11:

caaagttttcagggatacattgttttt atattttcaccacatgattttt cttctctccaatgtagTGGTCAGTTTTCTCTTGCAGTCGTCAGCCTGAA

CATAACATCCTTGGGATTACGCTCCCTCAAGGAGATAAGTGATGGAGAT

GTGATAATTTCAGGAAACAAAAATTTGTGCTATGCAAATACAATAAACT

GGAAAAAACTGTTTGGGACCTCCGGTCAGAAAACCAAAATTATAAGCAA

CAGAGGTGAAAACAGCTGCAgtaagtcaccgctttctgtttagtttatg gagttggttctaatgggtcctttatttgtatttagaatattgaagggct attcccatttaa;

wherein underwritten nucleotides correspond to the sequences identical (for SEQ ID NO: 6) or complementary (for SEQ ID NO: 7) to the primers of the set, capital letters relate to exon 12 and non-capital are intron fragments.

Amplification was performed under the following conditions: 95° C. for 10 minutes; 40 cycles of 95° C., 1 minute, 60° C., 1'30" and 72° C. 1 minute; and a final extension of 10 minutes at 72° C.

Besides, it was performed a Fluorescence in situ Hybridization (FISH). FISH was performed whenever there was sufficient remaining material following analysis of mutations. Amplification of EGFR was assessed by fluorescent in situ hybridization (FISH) using the LSI EGFR/CEP7 probe (Abbott Molecular Inc., DesPlaines, Ill.), as previously described (for example in document such as Salido et al., "Increased ALK gene copy number and amplification are frequent in non-small cell lung cancer", J Thorac Oncol—2011, Vol. No. 6, pp.:21-7). KRAS amplification was analyzed using a dual colour FISH assay with KRAS/CEP12 probe (Abnova). Samples with a ratio KRAS/CEP12 greater than 3, in at least 10% of 50 analysed nuclei were scored. When the average number of chromosome 12 exceeded 2.5 or 4 per cell, the case was considered polysomic or high-polysomic respectively.

Example 2

Presence of R451C and K467T EGFR Mutations and Acquired Resistance to Cetuximab

As depicted in FIG. 1, which is a plot of two different displays of a Next Generation Sequencing (NGS) 454 GS Junior platform (Roche Applied Science, Mannheim, Germany), shows that some patients acquired mutations in EGFR ectodomain following treatment with cetuximab. FIG. 1(A) shows a patient #31, in which the post-treatment tumor sample had acquired an A→C substitution at nucleotide 1400 of EGFR gene that was not present in the pre-treatment biopsy, causing a substitution of a lysine to a threonine at amino acid 467 (K467T). The substitution is detected by the genotyping method and visualized (arrow) by means of a double pick (band or curve) in this position. Lower pick corresponded to the C nucleotide.

On the other side, in FIG. 1 (B) it is shown the display of the sequencing process (Read minus the Reference) from patient #35, in which a C→T substitution at nucleotide 1351 of the EGFR gene was detected in the post-treatment sample, leading to a substitution of a arginine to a cysteine at amino acid 451 (R451C). Substitution is also marked with an arrow and in this case the change is visualized by a negative value.

Example 3

Mutations in SEQ ID NO: 12 (Fragment from Amino Acid 450 to Amino Acid 470 of SEQ ID NO: 2) Involve Resistance to Cetuximab Treatment 3A: EGFR Ectodomain Mutations and Acquired Resistance to Cetuximab in CRC Cell Models It was previously reported that acquisition of resistance in CRC cells is associated with emergence of KRAS, BRAF and NRAS activating mutation. To discover additional mechanisms of resistance to EGFR blockade 5 CRC cell lines were exploited (DiFi, LIM1215, HCA-46, NCIH508, OXCO-2 and CCK81), which are highly sensitive to cetuximab. All these cell lines are wild type for KRAS, NRAS, BRAF and PIK3CA with the exception of NCIH508, which displays the p.E545K PIK3CA mutation. Altogether, these cell models recapitulate the molecular features of tumors from CRC patients likely to respond to anti EGFR therapies. For each line, at least five million cells were exposed continuously to cetuximab until resistant populations emerged. To define molecular mechanisms underlying acquisition of resistance, it was initially performed Sanger sequencing of genes involved in regulation of the EGFR signalling pathway (EGFR, KRAS, BRAF, NRAS, and PIK3CA). In accordance with previous reports, resistant populations often displayed KRAS, BRAF and NRAS mutations (See Misale et al. "Blockade of egfr and mek intercepts heterogeneous mechanisms of acquired resistance to anti-egfr therapies in colorectal cancer", Sci Transl Med—2014; 6:224ra226). All of these alleles were detected in the resistant cells but not in the corresponding parental population from which they originated. Importantly, in several occasions multiple genetic alterations were concomitantly present in the resistant cell population indicating their polyclonal status. To assess the molecular features of individual clones it was therefore performed limited cell dilutions of LIM1215 and CCK81 as these cell lines are amenable to this procedure. Single clones were then subjected to Sanger sequencing for candidate genes (EGFR, KRAS, BRAF, NRAS, and PIK3CA). Notably, mutation profiling of clones identified three novel EGFR variants: S464L, G465R and I491M. Mutations S464L, G465R, together with mutations of Example 2 (R541C and K467T) are located in SEQ ID NO: 12 (a fragment defining part of the cetuximab binding epitope). Considering that the resistant derivatives are polyclonal, and in light of the limited sensitivity of the Sanger sequencing method, it was postulated that variants present in less than 20% of the cell populations might have remained undetected. To identify mutations present at low frequency it was employed droplet digital PCR (ddPCR) which is known to have a mutant/wild type sensitivity of 1:20000. ddPCR probes were designed and individually validated using control mutant DNA to detect EGFR variants previously identified in tumor biopsy or cell lines. This analysis unveiled the presence 3 new EGFR variants (S464L, G465R, and I491M) that were not detected by Sanger sequencing in resistant cell populations. ddPCR could not be performed in tissue samples because there was no sufficient material left. Overall, the mutational landscape of cell lines with acquired resistance to cetuximab, recapitulate the molecular profiles of tumors that relapsed upon cetuximab treatment.

ddPCR™ Supermix for Probes (Bio-Rad) using KRAS, NRAS, BRAF and EGFR assay (PrimePCR™ ddPCR™ Mutation Assay, Bio-Rad and custom designed). ddPCR was performed according to manufacturer's protocol and the results reported as percentage or fractional abundance of mutant DNA alleles to total (mutant plus wild type) DNA alleles. 8 to 10 µl of DNA template was added to 10 µl of ddPCR™ Supermix for Probes (Bio-Rad) and 2 µl of the primer/probe mixture. This 20 µl sample was added to 70 µl of Droplet Generation Oil for Probes (Bio-Rad) and used for droplet generation. Droplets were then thermal cycled with the following conditions: 5 minutes at 95° C., 40 cycles of 94° C. for 30 s, 55° C. for 1 minute followed by 98° C. for 10 minutes (Ramp Rate 2° C./sec). Samples were then transferred to a QX200™ Droplet Reader (Bio-Rad) for fluorescent measurement of FAM and HEX probes. Gating was performed based on positive and negative controls, and mutant populations were identified. Fractional Abundances of the mutant DNA in the wild-type DNA background were calculated for each sample using QuantaSoft software (Bio-Rad). Multiple replicates (minimum of four) were performed for each sample. ddPCR analysis of normal control gDNA from cell lines and no DNA template (water) controls were performed in parallel with all the samples, including again multiple replicates as a contamination-free control.

EGFR probes and primers sequences are available upon request.

Cell culture and generation of resistant cells utilized herein has already been previously described (see Misale S et al. Emergence of KRAS mutations and acquired resistance to anti-EGFR therapy in colorectal cancer. Nature. 2012; 486:532-6; Misale S, Arena S et al Blockade of EGFR and MEK intercepts heterogeneous mechanisms of acquired resistance to anti-EGFR therapies in colorectal cancer. Sci Transl Med. 2014; 6:224ra26). CCK81 cells were cultured in MEM medium (Invitrogen) supplemented with 5% FBS, 2 mM L-glutamine, antibiotics (100 U/mL penicillin and 100 mg/mL streptomycin) and grown in a 37° C. and 5% CO2 air incubator. CCK81 cetuximab-resistant derivatives were obtained by increasing the cetuximab dosage stepwise from 680 nM to 1.4 µM during the course of six months.

3B: Presence of S464L, G465R and K467T EGFR Mutation and Resistance to Cetuximab To establish whether the S464L, G465R and K467T EGFR mutations of the invention were responsible for the observed resistance to cetuximab, full-length wild-type EGFR and any of the S464L, G465R or K467T EGFR mutations were ectopically expressed in cultured NIH3T3 mouse embryonic fibroblast cell line that lack detectable endogenous EGFR expression.

Figure 2:
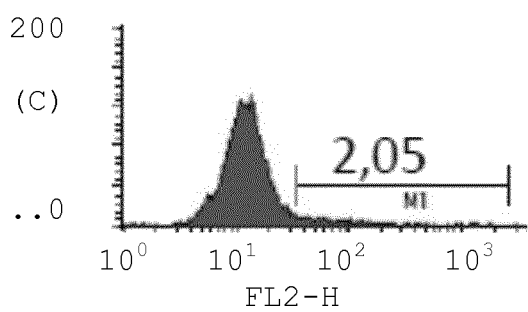
FIG. 2 is a Flow cytometry binding analysis of trypsinized NIH3T3 overexpressing wild-type EGFR (wt EGFR) and K467T EGFR mutant incubated with cetuximab (FIG. 2A) or panitumumab (FIG. 2B) as primary antibodies and using a secondary antibody conjugated with phycoerythrin directed against human IgG. C means counts; FL2H denotes the maximal signal intensity in the second channel of fluorescence detection with a band pass of 585±21 that is used to detect the phycoerythrin (PE) fluorescence; E means empty.
Figure 2:
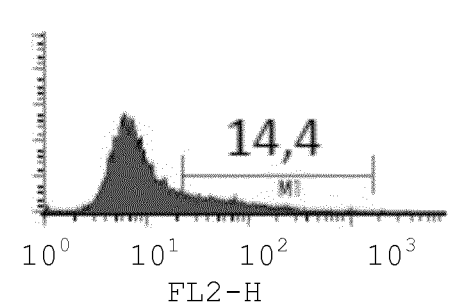
Figure 2:
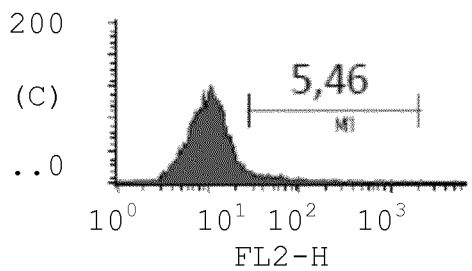
Figure 2:
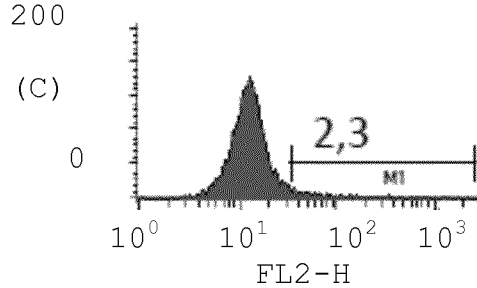
Figure 2:
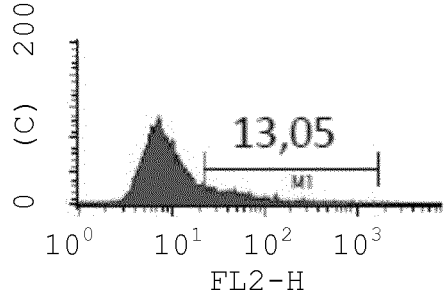
Figure 2:
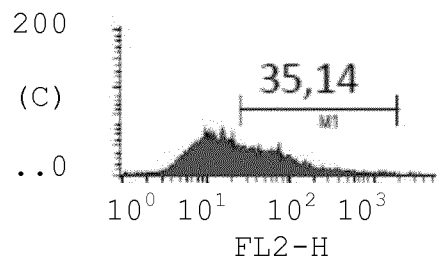
Figure 3:
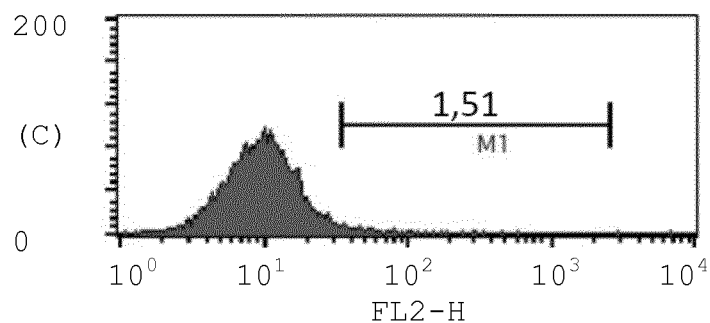
FIG. 3 is also a Flow cytometry binding analysis of trypsinized NIH3T3 overexpressing wild-type EGFR (wt EGFR) and S464L EGFR mutant incubated with cetuximab (FIG. 3A) or panitumumab (FIG. 3B) as primary antibodies and using a secondary antibody conjugated with phycoerythrin directed against human IgG. C means counts; FL2H denotes the maximal signal intensity in the second channel of fluorescence detection with a band pass of 585±21 that is used to detect the phycoerythrin (PE) fluorescence; E means empty.
Figure 3:
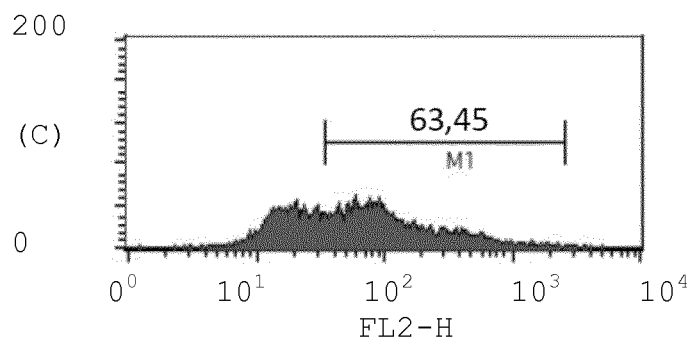
Figure 3:
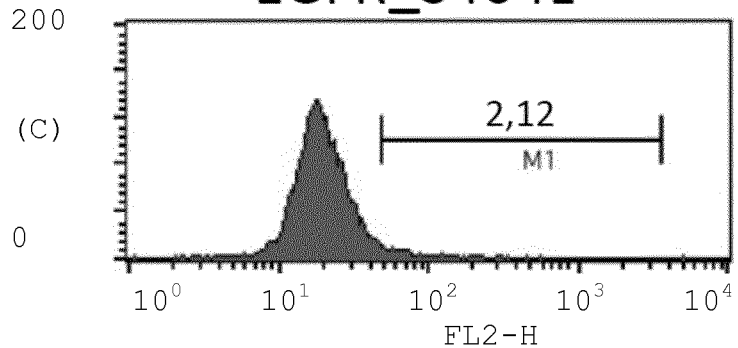
Figure 4:
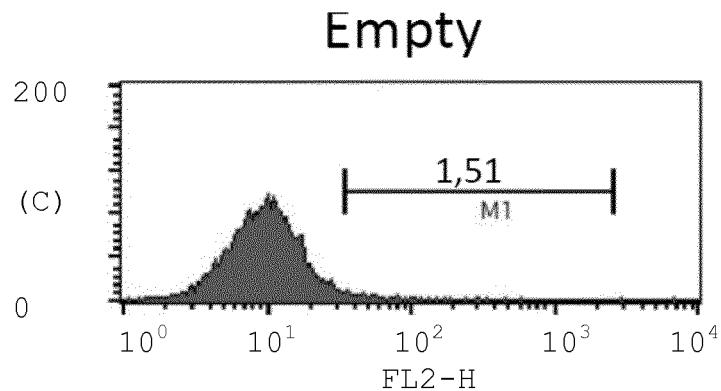
FIG. 4 shows a Flow cytometry binding analysis of trypsinized NIH3T3 overexpressing wild-type EGFR (wt EGFR) and G465R EGFR mutant incubated with cetuximab (FIG. 4A) or panitumumab (FIG. 4B) as primary antibodies and using a secondary antibody conjugated with phycoerythrin directed against human IgG. C means counts; FL2H denotes the maximal signal intensity in the second channel of fluorescence detection with a band pass of 585±21 that is used to detect the phycoerythrin (PE) fluorescence; E means empty.
Figure 4:
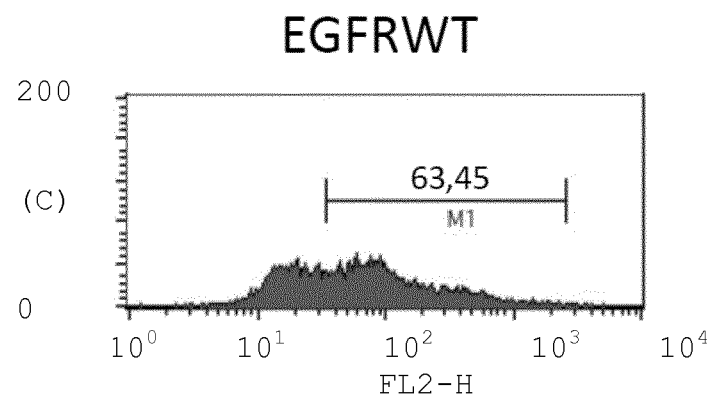
Figure 4:
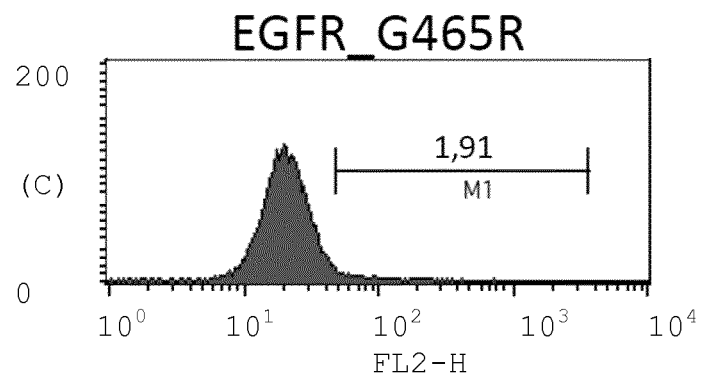

EGFR was stimulated with its natural ligand EGF in the presence of cetuximab or panitumumab in transfected cells. Antibody binding was analyzed by flow cytometry using a secondary antibody to human IgG conjugated with phycoerythrin (PE). NIH 3T3 cells expressing the empty vector were used as a negative control (EMPTY). The percentage of cells binding to the antibody are shown in the two-dimensional dot plots of FIGS. 2-4. In this FIGS. 2-4, cell counts (C of "counts", Y-axis) in the FL2H channel of the fluorescence detection are plotted for the assay with cetuximab (FIGS. 2A, 3A and 4A) and for the assay with panitumumab (FIGS. 2B, 3B and 4B).

In wild-type EGFR cells (EGFRWT in FIGS. 2-4A/B), both cetuximab and panitumumab inhibited EGFR activation, whereas in cells carrying the K467T mutation (EGFR_K467T in FIG. 2A/B), S464L (EGFR_S464L in FIG. 3A/B) and G465R (EGFR_G465R in FIG. 4A/B) panitumumab, but not cetuximab, effectively blocked EGF-induced EGFR activation. EMPTY is the negative control (EGFR non-expressing cells)

For the DNA constructs, the pLX301-EGFR WT construct, a generous gift from Dr. C. Sun and Prof R. Bernards (NKI, Amsterdam), was constructed from pLX301 (Addgene®). EGFR mutants containing the 4 point mutations (R451C, S464L, G465R, and K467T) were constructed using the QuikChange® II site-directed mutagenesis kits from Agilent Technologies with pLX301-EGFR WT plasmid as the template DNA. The presence of mutations was confirmed by DNA sequencing.

REFERENCES CITED IN THE APPLICATION

Mendelsohn J, Baselga J et al., "Epidermal growth factor receptor targeting in cancer". Semin Oncol—2006, Vol. 33, pp.: 369-38.

Lynch T J et al., "Activating mutations in the epidermal growth factor receptor underlying responsiveness of non-small-cell lung cancer to gefitinib", N Engl J Med-2004, Vol. 350, pp: 2129-2139.

Misale et al., "Emergence of KRAS mutations and acquired resistance to anti-EGFR therapy in colorectal cancer", Nature—2012, Vol. No. 486, pp.: 532-536.

Montagut et al., "Identification of a mutation in the extracellular domain of the Epidermal Growth Factor Receptor conferring cetuximab resistance in colorectal cancer", Nature medicine—2012, Vol. No. 18, pp.:221-223.

Voigt et al., "Functional Dissection of the Epidermal Growth Factor Receptor Epitopes Targeted by Panitumumab and Cetuximab", Neoplasia—2012, Vol. No. 14(11), pp.: 1023-1031.

Karapetis et al., "K-ras Mutations and Benefit from Cetuximab in Advanced Colorectal Cancer", The New England Journal of Medicine—2008, Vol. 359, pp.: 1757-1765.

Eisenhauer et al., "New response evaluation criteria in solid tumours: revised RECIST guideline (version 1.1)", Eur J Cancer 2009, Vol. 45(2):228-247.

Salido et al., "Increased ALK gene copy number and amplification are frequent in non-small cell lung cancer", J Thorac Oncol—2011, Vol. No. 6, pp.:21-7.

Diaz et al. "The molecular evolution of acquired resistance to targeted EGFR blockade in colorectal cancers", Nature-2012, Vol No. 486, pp.:537-40.

Misale et al. "Blockade of egfr and mek intercepts heterogeneous mechanisms of acquired resistance to anti-egfr therapies in colorectal cancer", Sci Transl Med-2014; 6:224ra226.

The invention claimed is:

1. An in vitro method of determining the suitability of a therapy regimen for a human subject suffering from cancer, wherein the method comprises:
   (a) determining the presence in a sample taken from the subject are selected from the group consisting of:
      (i) a change from arginine to cysteine at position 451 of SEQ ID NO: 2;
      (ii) a change from serine to leucine at position 464 of SEQ ID NO: 2;
      (iii) a change from glycine to arginine at position 465 of SEQ ID NO: 2; and
      (iv) a change from lysine to threonine at position 467 of SEQ ID NO: 2; and
   (b) administering panitumumab and not cetuximab to the subject;
   wherein the determining step of step (a) is carried out using a genotyping method comprising a set of primers allowing amplification of the genomic region encoding a fragment comprising position 450 to position 470 of SEQ ID NO: 2.

2. The in vitro method according to claim 1, wherein the set of primers consists of SEQ ID NO: 6 (CAAAGTTTTCAGGGATACATTGTTTTT) and SEQ ID NO: 7 (TTAAATGGGAATAGCCCTTCAATATT).

3. The in vitro method according to claim 1, wherein step (a) further comprises determining the presence of an arginine at position 492 of the amino acid sequence corresponding to SEQ ID NO: 2, and wherein the presence of the arginine at position 492 identified in step (a) is correlated with resistance of the subject to the therapy regimen comprising cetuximab.

4. An in vitro method of identifying, in a sample taken from a human subject, the presence of one or more amino acids in the EGFR amino acid sequence corresponding to SEQ ID NO: 2, wherein the one or more amino acids are selected from the group consisting of: a cysteine at position 451, a leucine at position 464, an arginine at position 465, and a threonine at position 467, wherein the method comprises determining the sequence of the EGFR protein, at least from position 450 to position 470 with a set of primers that amplifies a genomic region encoding the fragment comprising position 450 to position 470 of the EGFR protein.

5. An in vitro genotyping method of identifying, in a sample taken from a human subject, a presence or absence of an amino acid in the EGFR amino acid sequence corresponding to SEQ ID NO: 2 at one or more positions selected from the group consisting of: position 451, position 464, position 465, and position 467, wherein the method comprises providing one or more synthetic oligonucleotides that are specific to a codon encoding one or more amino acids selected from the group consisting of:
- (a) a cysteine at position 451 of SEQ ID NO: 2;
- (b) a leucine at position 464 of SEQ ID NO: 2;
- (c) an arginine at position 465 of SEQ ID NO: 2; and
- (d) a threonine at position 467 of SEQ ID NO: 2.

6. The in vitro method according to claim 5, wherein the method comprises PCR.

7. The in vitro method according to claim 5, wherein the one or more synthetic oligonucleotides hybridize with a nucleotide sequence or its complement, wherein said nucleotide sequence encodes a variant of SEQ ID NO: 13 comprising at least one amino acid selected from the group consisting of:
- (a) a cysteine at position 1 of SEQ ID NO: 13;
- (b) a leucine at position 14 of SEQ ID NO: 13;
- (c) an arginine at position 15 of SEQ ID NO: 13; and
- (d) a threonine at position 17 of SEQ ID NO: 13.

8. The in vitro method according to claim 5, wherein the one or more synthetic oligonucleotides hybridize with a nucleotide sequence or its complement, wherein said nucleotide sequence comprises one or more nucleotide changes as mapped to the nucleotide sequence of the EGFR variant 1 of SEQ ID NO.3, wherein the one or more nucleotide changes are selected from the group consisting of:
- (a) a change C to T at nucleotide 1351 counted from the start codon ATG at position 247 in SEQ ID NO:3 (C1597T);
- (b) a change C to T at nucleotide 1391 counted from the start codon ATG at position 247 in SEQ ID NO:3 (C1637T);
- (c) a change G to A at nucleotide 1393 counted from the start codon ATG at position 247 in SEQ ID NO:3 (G1639A); and
- (d) a change A to C at nucleotide 1400 counted from the start codon ATG at position 247 in SEQ ID NO:3 (A1646C).

9. The in vitro method according to claim 4, wherein the set of primers consists of SEQ ID NO: 6 (CAAAGTTTTCAGGGATACATTGTTTTT) and SEQ ID NO: 7 (TTAAATGGGAATAGCCCTTCAATATT).

10. The in vitro method according to claim 1, wherein in determining in a sample taken from the subject, the one or more mutations are selected from the group consisting of:
- (i) a change from serine to leucine at position 464 of SEQ ID NO: 2;
- (ii) a change from glycine to arginine at position 465 of SEQ ID NO: 2; and
- (iii) a change from lysine to threonine at position 467 of SEQ ID NO: 2; and
administering panitumumab and not cetuximab to the subject.

11. The in vitro method of claim 4, wherein the one or more amino acids in the EGFR amino acid sequence corresponding to SEQ ID NO: 2, are selected from the group consisting of: a leucine at position 464, an arginine at position 465, and a threonine at position 467.

12. The in vitro genotyping method according to claim 5 wherein the codon encoded one or more amino acids are selected from the group consisting of:
- (a) a leucine at position 464 of SEQ ID NO: 2;
- (b) an arginine at position 465 of SEQ ID NO: 2; and
- (c) a threonine at position 467 of SEQ ID NO: 2.

* * * * *